United States Patent [19]
Etschenberg et al.

[11] 4,310,517
[45] * Jan. 12, 1982

[54] TUMOR-RESOLVING AND HISTOLYTIC MEDICAMENTS AND THEIR USE

[75] Inventors: Eugen Etschenberg; Wolfgang Opitz; Siegfried Raddatz, all of Cologne, Fed. Rep. of Germany

[73] Assignee: Troponwerke GmbH & Co., KG, Cologne, Fed. Rep. of Germany

[*] Notice: The portion of the term of this patent subsequent to Jun. 30, 1998, has been disclaimed.

[21] Appl. No.: 82,450

[22] Filed: Oct. 9, 1979

Related U.S. Application Data

[63] Continuation-in-part of Ser. No. 862,896, Dec. 21, 1977, abandoned.

[30] Foreign Application Priority Data

Dec. 28, 1976 [DE] Fed. Rep. of Germany ....... 2659154
Oct. 11, 1977 [DE] Fed. Rep. of Germany ....... 2745673

[51] Int. Cl.$^3$ ..................... A61K 37/00; C07C 103/52
[52] U.S. Cl. .............................. 424/177; 260/112.5 R
[58] Field of Search .................. 424/177; 260/112.5 R

[56] References Cited

PUBLICATIONS

Rich, et al., J. C. S. (1974), 897–898.
Riordan, et al, Tetrahedron Letters, No. 16, 1247–1250, (1976).
Bodanszky, et al., Chem. Abstr. 72, 1970, 83007+.
Weiner, et al., J. A. C. S. 88, (1966), 3851–3859.
Doherty, et al., J. Biol. Chem. 147, (1943), 617–637.
Benoiton, et al., J. Chem. Soc. (1964), 824–836.
Patchornik, et al., J. A. C. S. 86, 1860–1861, (1964).

Primary Examiner—Delbert R. Phillips
Attorney, Agent, or Firm—Sprung, Felfe, Horn, Lynch & Kramer

[57] ABSTRACT

Dehydrooligopeptides, some of which are known, demonstrate histolytic and tumor-resolving activity and may be used in medicaments causing the lysis of animal tissues and/or tumors in warm-blooded animals.

14 Claims, No Drawings

TUMOR-RESOLVING AND HISTOLYTIC MEDICAMENTS AND THEIR USE

This is a continuation-in-part application of Ser. No. 862,896 filed Dec. 21, 1977, now abandoned.

The present invention relates to the use as histolytic medicaments, of dehydrooligopeptides, some of which are known.

In the following text, dehydrooligopeptides are to be understood as compounds which are linked in a peptide-like manner and consist of from two to ten aminoacid units and which have at least one double bond (corresponding to at least one dehydroaminoacid group).

The use of dehydrooligopeptides as medicaments has not previously been disclosed.

It is known that a histolytic action can be achieved with substances of the most diverse nature. However, the general toxicity of such compounds is usually so high that practical treatment regimens which can be easily manipulated therapeutically and which do not harm the patients even further scarcely exist.

Existing commercial products for use for corresponding indications are cytostatic agents, and cyclophosphamide may be mentioned here as an example.

All the agents used hitherto exhibit an extremely high general toxicity. This is frequently so pronounced that it becomes necessary to interrupt therapy and thus the tumour diseases often end fatally.

The action of cyclophosphamide may be mentioned here as an example of the generally toxic action. Thus, M. H. N. TATTERSALL and J. S. TOBIAS report in The Lancet 1976/II, No. 7994, page 1,071: "In the case of many anti-cancer agents, twice the dose which kills 10% of the animals ($LD_{10}$) is fatal for 90% of the animals ($LD_{90}$). FREI and FREIREICH (Advances in Chemotherapy 2 (1965), 269) were able to demonstrate the significance of using agents such as cyclophosphamide in dosages which approached the toxicity rate ($LD_{10}$). The decisive characteristic of these experiments was the exponential increase observed in cell destruction with a low (arithmetic) increase in dose. The $LD_{10}$ dosage of cyclphosphamide destroyed 99.999% of the tumour cells, but one eighth of this dose (which was far less toxic) destroyed only 90% of the tumour cells and was therefore less active clinically by 5 log.

This observation is the reason for the generally widely-held view that chemotherapy of cancer is only effective when it is not generally toxic."

The present invention thus relates to the use of dehydrooligopeptides, some of which are known, as medicaments with a histolytic action, which substantially avoid the above mentioned disadvantages of generally toxic actions; they are distinguished by a powerful histolytic action, which depends on the dose used, coupled with good general tolerance.

It has been found that the compounds which are dehydrooligopeptides and their salts possess a very good histolytic action in transplated tumours.

In particular, it has been found that compounds which are dehydrooligopeptides of the following general formula I and their salts

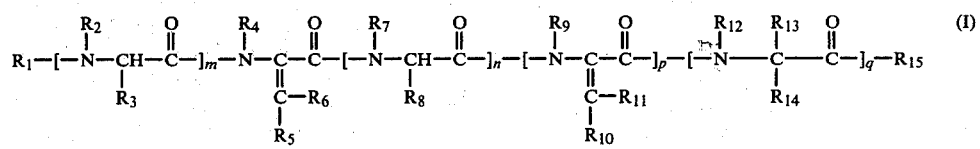

in which $R_1$ is a hydrogen atom, optionally substituted alkanoyl, optionally substituted alkenoyl, alkoxycarbonyl, optionally substituted aroyl, optionally substituted aralkanoyl or aralkenoyl, aralkoxycarbonyl, carbamoyl, optionally substituted hetero-aroyl, optionally substituted lower alkylsulphonyl or optionally substituted arylsulphonyl, $R_2$, $R_7$ and $R_{12}$ are the same or different and each is a hydrogen atom or a lower alkyl group, $R_3$, $R_8$ and $R_{13}$ are the same or different and each is a hydrogen atom, straight-chain or branched optionally substituted lower alkyl, optionally substituted aryl optionally substituted aralkyl or aralkenyl, optionally substituted cycloalkyl or cycloalkenyl, indolylmethyl or an optionally substituted heterocyclic-methyl group having from four to seven ring members and one or two hetero-atoms, or one or more of $R_2$, $R_7$ and $R_{12}$, together with, in each case, the adjacent substituent $R_3$, $R_8$ or $R_{14}$ respectively, form(s) a divalent alkylene chain having three or four carbon atoms, $R_4$ and $R_9$ each represent a hydrogen atom or a lower alkyl group, and $R_5$ and $R_{10}$ are the same or different and each is a hydrogen atom or optionally substituted lower alkyl, $R_6$ and $R_{11}$ are the same or different and each is optionally substituted alkyl, optionally substituted aryl, an optionally substituted heterocyclic radical having from five to seven ring members and one or two hetero-atoms, optionally substituted aralkyl or optionally substituted aralkenyl, or $R_6$ and/or $R_{11}$, together with $R_5$ or $R_{10}$, respectively, represent an optionally substituted alkylene or alkylene chain having from three to seven carbon atoms, $R_{14}$ is a hydrogen atom or optionally substituted lower alkyl or, together with $R_{13}$ and the carbon atom between them, represents an alicyclic radical having from four to seven carbon atoms, $R_{15}$ is hydroxyl, optionally substituted lower alkoxy or alkenyloxy, optionally substituted lower alkylthio or alkenylthio, optionally substituted arylthio, optionally substituted hydrazino, amino, optionally substituted lower alkylamino or dialkylamino or alkenylamino or dialkenylamino or alkinylamino, optionally substituted arylamino, optionally substituted mono- or di-aralkylamino, a nitrogen-containing optionally substituted hetero-cyclic radical having from four to seven ring members, optionally containing one or two further hetero-atoms, amino substituted by one or more optionally substituted alicyclic radicals having from three to seven ring members, or aralkyloxyamino, and m, n, p and q are the same or different and each represents a FIG. 0 or 1, with the proviso that m, n, p and q may not all be 1 at the same time, have powerful histolytic properties.

Substances which are closely related chemically to the dehydrooligopeptides and which have a comparable action have not hitherto been disclosed.

It is new and completely surprising that dehydrooligopeptides display such a highly pronounced histolytic action.

The active compounds according to the invention are thus an enrichment of pharmacy.

In the general formula (I), the radicals $R_1$ to $R_{15}$ have the following preferred meanings:

An alkanoyl radical $R_1$ is preferably straight-chain or branched alkanoyl having from two to six carbon atoms. Examples which may be mentioned are: acetyl, propionyl, butyryl and pentanoyl.

An alkenoyl radical $R_1$ is preferably straight-chain or branched alkenoyl having from three to six carbon atoms. Examples which may be mentioned are: crotonyl and acrylyl.

Possible substituents of $R_1$ for the alkanoyl or alkenoyl radical $R_1$ are preferably: from one to three halogen atoms, preferably fluorine and chlorine atoms, methoxy, ethoxy and hetero-aryl. Examples which may be mentioned are chloroacetyl, trichloroacetyl, trifluoroacetyl and thiophenyl.

The straight-chain or branched lower alkoxycarbonyl radical $R_1$ is preferably methoxy, ethoxy, propoxy or butoxycarbonyl, especially tert.-butoxycarbonyl.

The optionally substituted aroyl radical $R_1$ is preferably benzoyl or naphthoyl.

The optionally substituted aralkanoyl or aralkenoyl radical $R_1$ preferably has from eight to twelve carbon atoms, in particular from eight to ten carbon atoms. Examples which may be mentioned are phenacetyl, phenpropionyl, phenisopropionyl, cinnamoyl, $\beta$-methylcinnamoyl and phenylbutanoyl.

Possible substituents in the aroyl, aralkanoyl or aralkenoyl radical $R_1$ are: from one to three halogen atoms, alkyl or alkoxy having up to three carbon atoms, especially methoxy, trifluoromethyl, nitro or hydroxyl, optionally acylated with a lower organic acid radical.

The aralkoxycarbonyl radical $R_1$ denotes, in particular, aralkoxycarbonyl having from eight to ten carbon atoms, most preferably the benzyloxycarbonyl group.

An optionally substituted hetero-aroyl radical $R_1$ is understood as a heterocyclic radical which has five to seven ring members and can contain from one to three hetero atoms which are the same or different and each of which is a nitrogen, sulphur or oxygen atom and on which there is a carbonyl group. Examples of this radical which may be mentioned are pyridinecarbonyl, thiophenecarbonyl, furanecarbonyl, pyrrolecarbonyl, oxazolecarbonyl, thiazolecarbonyl and pyrazinecarbonyl, optionally substituted by one or more halogen atoms, preferably fluorine and/or chlorine atoms, alkoxy having from one to four carbon atoms or alkyl having from one to four carbon atoms.

The optionally substituted lower alkylsulphonyl radical $R_1$ or arylsulphonyl radical $R_1$ preferably denotes methanesulphonyl or ethanesulphonyl, or benzenesulphonyl or toluenesulphonyl, respectively.

A lower alkyl group as a radical $R_2$, $R_7$ or $R_{12}$ preferably denotes methyl or ethyl.

If $R_2$, $R_7$ and $R_{12}$, together with, in each case, the adjacent substituent $R_3$, $R_8$ or $R_{14}$, respectively, form an alkylene chain with three to four carbon atoms, this means that $R_2$ forms a pyrrolidine or piperidine ring with the associated nitrogen atom, the adjacent —CH— group of the chain and $R_3$. Similarly in the case of $R_7$ and $R_8$ and, respectively, $R_{12}$ and $R_{13}$.

A lower alkyl group as the radicals $R_4$ and $R_9$ preferably denotes methyl or ethyl.

An optionally substituted straight-chain or branched lower alkyl or alkenyl radical $R_3$, $R_8$ and $R_{13}$ denotes a hydrocarbon radical, preferably having from one to six carbon atoms and optionally a double or triple bond, such as, for example, methyl, ethyl, propyl, isopropyl, butyl, isobutyl, sec.-butyl or tert.-butyl, pentyl and hexyl with their possible isomers, and furthermore vinyl, ethinyl, propenyl or crotyl.

Substituents of the alkyl radical $R_3$, $R_8$ or $R_{13}$ which may be mentioned are: from one to three halogen atoms, hydroxyl groups, alkoxy groups having preferably from one to four carbon atoms, alkylthio groups having preferably from one to four carbon atoms, sulphhydryl groups, carbamido groups and carboxyl groups.

Examples which may be mentioned of such substituted alkyl groups are carboxymethyl, carboxyethyl, carbamoylmethyl, methylmercaptoethyl, trifluoromethyl, fluoromethyl, chloromethyl and hydroxymethyl.

An optionally substituted aryl group $R_3$, $R_8$ and $R_{13}$ in the general formula I is preferably phenyl optionally substituted by one or more halogen atoms, trifluoromethyl groups, hydroxyl groups, lower alkoxy groups having from one to four carbon atoms, alkyl groups having from one to four carbon atoms, nitro groups or lower acyloxy groups having from one to four carbon atoms.

An optionally substituted aralkyl or aralkenyl group $R_3$, $R_8$ and $R_{13}$ preferably denotes phenylalkyl or phenylalkenyl having up to four carbon atoms and optionally a double or triple bond in the side chain, in particular a $CH_2$ group. The aralkyl or aralkenyl radical can be substituted by one or more halogen atoms, nitro, hydroxyl or methoxy or alkyl having from one to four carbon atoms.

An optionally substituted cycloalkyl or cycloalkenyl radical $R_3$, $R_8$ or $R_{13}$ represents monocyclic, bicyclic and tricyclic cycloalkyl or cycloalkenyl having preferably from 3 to 10, in particular 3, 5 or 6, carbon atoms. Examples which may be mentioned are optionally substituted cyclopropyl, cyclopropenyl, cyclobutyl, cyclopentyl, cyclopentenyl, cyclohexyl, cyclohexenyl, cycloheptyl, bicyclo[2.2.1]heptyl, bicyclo[2.2.2]octyl and adamantyl.

The cycloalkyl or cycloalkenyl radical $R_3$, $R_8$ or $R_{13}$ can be substituted by one or more halogen atoms, nitro or hydroxyl groups, or alkoxy or alkyl groups having from one to four carbon atoms in each case.

An optionally substituted heterocyclic-methyl group denotes, in particular, furfuryl, thenyl, pyrrolylmethyl, thiazolylmethyl, oxazolylmethyl, pyridinemethyl, piperidinemethyl, pyrazinemethyl or morpholinemethyl, optionally substituted by from one to three halogen atoms or alkyl or alkoxy groups having from one to three carbon atoms, or by one nitro group.

Optionally substituted lower alkyl radicals $R_5$, $R_{10}$ and $R_{14}$ denote alkyl having preferably from one to six, in particular one to two, carbon atoms, optionally substituted by halogen atoms, especially chlorine or fluorine atoms.

An optionally substituted alkyl group $R_6$ or $R_{11}$ in the general formula I denotes a straight-chain or branched alkyl group having preferably from one to six carbon atoms, in particular from one to three carbon atoms, optionally substituted by from one to three halogen atoms, preferably chlorine or fluorine atoms, or by alkoxy groups having from one to four carbon atoms, in particular methoxy groups.

An optionally substituted aryl radical $R_6$ or $R_{11}$ denotes, in particular, phenyl or naphthyl, optionally substituted by halogen atoms, preferably fluorine and chlorine atoms, alkyl or alkoxy groups having from one to four carbon atoms, methoxy and methyl groups being preferred, nitro groups, hydroxyl groups, lower acyloxy groups having from one to four carbon atoms or amino, lower alkylamino or lower dialkylamino groups, preferably dimethylamino groups.

An optionally substituted heterocyclic radical $R_6$ or $R_{11}$ denotes a heterocyclic radical having from five to seven ring members and one or two hetero-atoms each of which may be, in particular, nitrogen, sulphur or oxygen. Examples which may be mentioned are thienyl, furyl, pyrrolyl, pyridyl, imidazolyl, pyrazolyl, pyrimidyl, pyrazinyl and morpholinyl, optionally substituted by halogen atoms, alkyl or alkoxy groups having from one to four carbon atoms or hydroxyl, nitro or trifluoromethyl groups.

Optionally substituted aralkyl or aralkenyl groups $R_6$ and $R_{11}$ denote, in particular, those having from seven to ten carbon atoms; phenylalkyl or phenylalkenyl groups having from one to four carbon atoms in the aliphatic moiety are particularly preferred, for example cinnamenyl and phenethyl, said aralkyl and aralkenyl groups being optionally substituted by one or more halogen atoms, alkyl or alkoxy groups having preferably from one to four carbon atoms, nitro groups and trifluoromethyl groups.

In the general formula I, the radicals $R_6$ and $R_{11}$, together with $R_5$ and $R_{10}$ respectively, and the carbon atom, at the double bond, linking them, can form a cycloalkylidene ring or cycloalkenylidene ring having preferably from three to seven carbon atoms, in particular cyclohexylidene and cyclohexenylidene.

An optionally substituted lower alkoxy or alkenyloxy radical $R_{15}$ in the general formula I denotes a straight-chain or branched alkoxy or alkenyloxy radical having from one to six carbon atoms, in particular from one to four carbon atoms, for example, methoxy, ethoxy, propoxy, isopropoxy, butoxy, isobutoxy, sec.-butoxy or tert.-butoxy, said alkoxy and alkenyloxy radicals being optionally substituted by one or more halogen atoms or alkoxy groups having one or two carbon atoms.

A lower optionally substituted alkylthio or alkenylthio group $R_{15}$ is an alkylthio or alkenylthio group having from one to six carbon atoms, in particular from one to four carbon atoms. Substituents which may be mentioned are from one to three halogen atoms or alkoxy groups or a carboxyl group.

An optionally substituted arylthio group $R_{15}$ is preferably phenylthio, optionally substituted by one to three halogen atoms or lower alkyl or alkoxy groups having preferably one or two carbon atoms in each case.

An optionally substituted hydrazine radical $R_{15}$ means that the hydrazine radical can be substituted by lower alkyl, optionally substituted aryl, preferably by phenyl, optionally substituted in turn by from one to three halogen atoms or lower alkyl or alkoxy groups, or by a heterocyclic radical, having one or two nitrogen, oxygen and/or sulphur atoms, which in addition can be fused with a phenyl ring.

An optionally substituted lower monoalkylamino or monoalkenylamino or dialkenylamino or dialkylamino group $R_{15}$ denotes, in each case, such a group having a straight-chain and/or branched alkyl or alkenyl moiety(ies) having preferably from one to six carbon atoms, such as, for example, methylamino, ethylamino, pentylamino and 1,1-dimethyl-2-propinylamino. The optional substituent(s) may, for example, be halogen atoms, hydroxyl groups, alkoxy groups having one or two carbon atoms, an amino or lower monoalkylamino or dialkylamino group, a sulphonic acid radical or a phosphate radical or a heterocyclic radical, in particular a morpholine or imidazole ring.

An optionally substituted arylamino group $R_{15}$ preferably denotes phenylamino, optionally substituted by one to three halogen atoms or alkyl or alkoxy groups with preferably one or two carbon atoms in each case.

An optionally substituted monoaralkylamino or diaralkylamino group $R_{15}$ preferably denotes monophenylalkylamino or diphenylalkylamino, having from one to four carbon atoms in the aliphatic moiety in each case. The optional substituent(s) may be from one to three halogen atoms, or alkyl or alkoxy groups, having from one to four carbon atoms in each case.

A heterocyclic group, containing a nitrogen atom, $R_{15}$, denotes a heterocyclic group, containing a nitrogen atom, having from four to seven ring members, optionally containing one or two further hetero-atoms, and optionally substituted by lower alkyl, lower hydroxyalkyl or phenyl.

An amino group substituted by alicyclic radicals having from three to seven ring members, $R_{15}$, denotes cyclopropylamino, cyclobutylamino, cyclopentylamino, cyclohexylamino and cycloheptylamino group, preferably the cyclohexylamino, or the correspondingly di-substituted amino group. This can be substituted by lower alkyl, alkenyl, alkinyl or aryl groups.

Some of the starting compounds for the preparation of the compounds of the general formula I according to the invention, that is to say the corresponding 2,4-disubstituted 5(4H)-oxazolones, are known from the literature. If they are not known, they can be prepared by the methods described in the literature. The reaction of acetylglycine with benzaldehyde may be described here as an example. The reaction takes place according to the equation

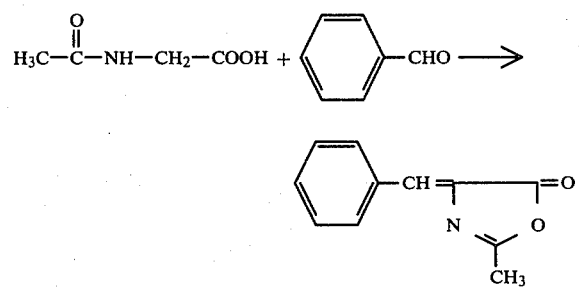

The reaction is carried out by mixing the two components in an equimolar ratio in the presence of a condensing agent, usually acetic anhydride, which conveniently at the same time serves as a solvent, and of a basic component, such as sodium acetate. After standing for several hours, the mixture is worked up by diluting with water and recrystallising the resulting 4-benzylidene-2-methyl-5(4H)-oxazolone, which has precipitated, from ethyl acetate/petroleum ether.

Further examples of starting compounds which may be mentioned are: 2-methyl-4-(2-thenylidene)-5(4H)-oxazolone, 2-methyl-4-(2-naphthylmethylene)-5(4H)-oxazolone, 4-(4-acetoxy-3-nitrobenzylidene)-2-methyl-5(4H)-oxazolone, 4-ethoxymethylene-2-phenyl-5(4H)-oxazolone, 4-cyclohexylmethylene-2-phenyl-5(4H)-oxazolone, 4-benzylidene-2-trifluoromethyl-5(4H)-oxazolone, 4-(1-methylpropylidene)-2-phenyl-5(4H)-oxazolone, 2-phenyl-4-(2-thenylidene)-5(4H)-oxazolone, 2-(3-pyridyl)-4-(2-thenylidene)-5(4H)-oxazolone, 4-(1-methyl-3-phenyl-2-propenylidene)-2-phenyl-5(4H)-oxazolone, 2-(1-acetamido-2-phenylvinyl)-4-(4-dimethyl-aminobenzylidene)-5(4H)-oxazolone, 4-thenylidene-2-(3-trifluoromethylphenyl)-5(4H)-oxazolone, 4-(2-cyclohexenylidene)-2-phenyl-5(4H)-oxazolone, 4-(3-phenyl-2-propylidene)-2-phenyl-5(4H)-oxazolone, 4-(α-methylbenzylidene)-2-phenyl-5(4H)-oxazolone, 4-cyclohexylidene-2-phenyl-5(4H)-oxazolone, 4-(3-chlorobenzylidene)-2-(1-acetamido-2-phenylethyl)-5(4H)-oxazolone, 4-(3-chlorobenzylidene)-2-(L-1-tert.-butoxycarbonylamino-2-phenylethyl)-5(4H)-oxazolone, 2-(1-acetamido-2-phenylvinyl)-4-(4-hydroxybenzylidene)-5(4H)-oxazolone, 2-(1-propenyl)-4-(2-thenylidene)-5(4H)-oxazolone, 2-ethoxymethyl-4-(2-thenylidene)-5(4H)-oxazolone, 2-phenyl-4-benzylidene-5(4H)-oxazolone, 2-(2-phenylvinyl)-4-benzylidene-5(4H)-oxazolone, 2-[1-acetamido-2-(2-thienyl)vinyl]-4-(2-thenylidene)-5(4H)-oxazolone, 2-[1-acetamido-2-(2-thienyl)vinyl]-4-(5-methylthenylidene-2)-5(4H)-oxazolone, 2-[1-acetamido-2-(2-thienyl)-vinyl]-4-(4-nitrobenzylidene)-5(4H)-oxazolone, 2-[2-(3,4,5-trimethoxyphenyl)vinyl]-4-(2-thenylidene)-5(4H)-oxazolone, 2-methyl-4-(5-nitrothenylidene-2)-5(4H)-oxazolone, 2-(2-thienyl)-4-(2-thenylidene)-5(4H)-oxazolone, 2-phenyl-4-(4-pyridylmethylene)5(4H)-oxazolone, 2-(4-nitrophenyl)-4-(2-thenylidene)-5(4H)-oxazolone, 2-(3-thienylmethyl-4-(2-thenylidene)-5(4H)-oxazolone and 2-[1-acetamido-2-(2-thienyl)vinyl]-4-(α-methyl-2-thienylidene)-5(4H)-oxazolone.

A number of the active compounds according to the invention are new; however, they can be prepared by known processes (compare D. G. DOHERTY et al., J. biol. Chem. 147 (1943), 617). They are obtained, for example, either by alkaline hydrolysis of the corresponding 2,4-disubstituted 5(4H)-oxazolones or by aminolysis of the oxazolones with the alkali metal salts, esters or amides of amioacids.

The reaction may be illustrated using the syntheses of N-acetyldehydrophenylalanyldehydro-(3-chlorophenyl)alanine and N-acetyldehydrophenylalanyldehydro-(3-chlorophenyl)alanyl-L-tyrosine as examples:

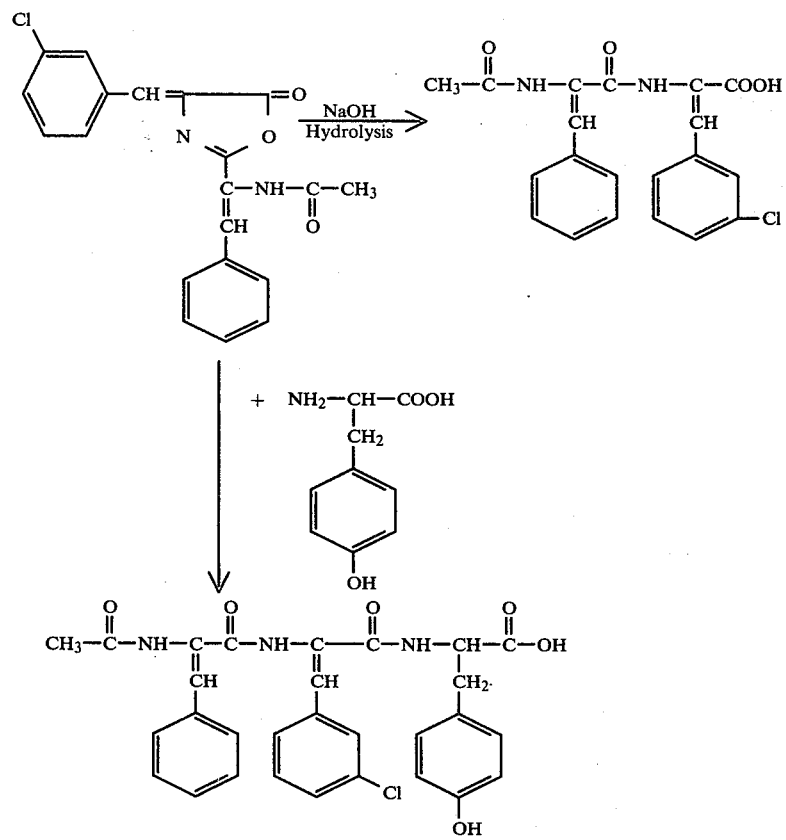

The reaction is usually carried out by stirring, or leaving the reactant or reactants to stand, in a diluent, such as aqueous acetone, tetrahydrofurane, dimethylformamide or an alcohol, usually at room temperature or a slightly elevated temperature, the reaction time depending on the reactivity of the reactants, for example, the reaction time may be from half an hour to twenty hours.

The mixture is worked up by acidifying with, for example, HCl, and evaporating off the organic solvent, whereupon the end product usually precipitates.

If the reaction times are extremely long, partial racemisation cannot be excluded, as can be seen from the optical rotation values of the products obtained.

In some cases it has proved to be appropriate, for reasons of purity and yield, to use an aminoacid ester instead of the free aminoacid in the aminolysis and to hydrolyse this ester after the condensation.

Examples which may be mentioned of the active compounds according to the invention are: N-benzoyldehydro-β-(2-thienyl)alanine methyl ester, N-acetyldehydro-β-(2-thienyl)alanine ethyl ester, N-acetyldehydrophenylalanine, N-phenylacetyldehydro-β-(thienyl)alanine, N-acetyl-DL-phenylalanyldehydro-(3-chlorophenyl)alanine, N-tert.-butoxycarbonyl-L-phenylalanyldehydro-(3-chlorophenyl)alanine, L-phenylalanyldehydro-(3-chlorophenyl)alanine, N-acetyldehydrophenylalanyl-L-proline, N-acetyldehydrophenylalanyl-D-proline, N-acetyldehydrophenylalanyl-L-tyrosine, N-acetyldehydrophenylalanyl-D-tyrosine, N-acetyldehydrophenylalanyl-L-leucine, N-acetyldehydrophenylalanyl-L-methionine, N-acetyldehydrophenylalanyl-L-aspartic acid, N-acetyldehydrophenylalanyl-L-glutamine, N-acetyldehydrophenylalanyl-DL-3-fluoroalanine, N-acetyldehydrophenylalanyl-L-serine, N-acetyldehydrophenylalanyl-L-tyrosine, N-acetyldehydrophenylalanylglycine, N-acetyldehydrophenylalanyl-L-(p-nitrophenyl)alanine, N-acetyldehydrophenylalanyl-DL-(p-chlorophenyl)alanine, N-trifluoroacetyldehydrophenylalanyl-L-tyrosine, N-acetyldehydro-(p-methylphenyl)alanyl-L-tyrosine, N-benzoyl-2-cyclohexylideneglycyl-L-tyrosine, N-benzoyl-2-(2-cyclohexenylidene)glycyl-L-tyrosine, N-acetyldehydro-3-(2-furyl)alanyl-L-tyrosine, N-acetyldehydro-3-cinnamenylalanyl-L-tyrosine, N-acetyldehydro-3-(2-naphthyl)-alanyl-L-tyrosine, N-benzoyldehydro-3-cyclohexylalanyl-L-tyrosine, N-benzoyldehydro-3-benzyl-3-methylalanyl-L-leucine, N-trifluoroacetyldehydrophenylalanyl-L-tyrosine tert.-butyl ester, N-benzoyldehydro-3-(2-thienyl)alanyl-L-proline, N-acetyldehydrophenylalanine (1-carboxy-1-cyclopentyl) amide, N-acetyldehydro-3-(2-thienyl)alanyl-L-tyrosine, N-phenacetyldehydro-3-(2-thienyl)alanyl-L-tyrosine tert.-butyl ester, N-phenacetyldehydro-3-(2-thienyl)alanyl-L-tyrosine, N-phenacetyldehydro-3-(2-thienyl)alanyl-L-leucine methyl ester, N-phenacetyldehydro-3-(2-thienyl)alanyl-L-leucine, N-benzoyldehydro-3-(2-thienyl)alanyl-L-tyrosine, N-benzoyldehydro-3-(2-thienyl)alanyl-L-(p-nitrophenyl)alanine, N-nicotinoyldehydro-3-(2-thienyl)alanyl-L-tyrosine, N-(3-trifluoromethylbenzoyl)dehydro-3-(2-thienyl)alanyl-L-tyrosine, N-benzoyldehydro-3-(2-thienyl)alanyl-L-proline, N-nicotinoyldehydro-3-(2-thienyl)alanyl-L-(p-nitrophenyl)alanine, N-benzoyl-3-methyl-3-(2-thienyl)-dehydroalanyl-L-tyrosine, N-acetyldehydro-3-(2-thienyl)alanyl-D-tyrosine, N-cinnamoyldehydrophenylalanylglycine, N-benzoyldehydro-3-(2-thienyl)alanyl-L-phenylalanine, N-benzoyldehydro-3-(2-thienyl)alanyl-L-leucine, N-acetyldehydro-3-(2-thienyl)-L-phenylalanine, N-acetyldehydro-3-(2-thienyl)alanyl-L-leucine, N-benzoyldehydro-3-(2-thienyl)alanyl-L-tyrosine methyl ester, N-acetyldehydro-3-(2-thienyl)alanyl-L-tyrosine methyl ester, N-benzoyldehydro-3-(2-thienyl)alanyl-L-tyrosine amide, N-benzoyldehydro-3-(2-thienyl)alanyl-L-tyrosine N'-hexylamide, N-benzoyldehydro-3-(2-thienyl)alanyl-L-tyrosine N'-cyclohexylamide, N-benzoyldehydro-3-(2-thienyl)alanyl-L-tyrosine N',N'-dimethylamide, N-benzoyldehydro-3-(2-thienyl)alanyl-L-tyrosine morpholide, N-acetyldehydrophenylalanyldehydrotyrosine, N-acetyldehydrophenylalanyldehydro-(p-nitrophenyl)alanine, N-acetyldehydrophenylalanyldehydro-(p-fluorophenyl)alanine, N-acetyldehydrophenylalanyldehydro-(4-dimethylaminophenyl)alanine, N-acetyldehydrophenylalanyldehydro-(3-chlorophenyl)alanine, N-acetyldehydrophenylalanyldehydro-(3-chlorophenyl)alanyl-L-tyrosine, N-acetyldehydrophenylalanyl-3-phenylserine, N-benzoyldehydrophenylalanylglycine, N-benzoyldehydrophenylalanyl-3-phenylserine, N-acetyldehydroleucylglycine, N-carbobenzoxyglycyldehydrophenylalanine, N-acetyldehydrophenylalanyl-L-alanine, N-acetyldehydrophenylalanyl-L-phenylalanine, N-acetyl-DL-phenylalanyldehydrophenylalanine, N-acetyl-dehydrophenylalanyldehydrophenylalanine, N-benzoyldehydrophenyl-alanyldehydrophenylalanine, N-benzoyldehydrophenylalanyldehydro-tyrosine, N-acetyldehydroleucyldehydrophenylalanine, N-carbobenzoxyglycyldehydrophenylalanyl-L-glutamic acid, N-carbobenzoxyglycycldehydrophenylalanyl-phenylserine, N-acetyldehydrophenyl-alanyldehydrophenylalanyl-L-alanine, -glycine, -L-leucine, -L-phenylalanine, -L-tyrosine, -L-proline, -3-phenylserine, -L-glutamic acid and -L-cystine, N-acetyldehydrophenylalanyl-D-glutamic acid, N-benzoyldehydro-3-(2-thienyl)alanyl-L-tyrosinebenzyl ester, N-benzoyldehydro-3-(2-thienyl)-L-tyrosine N-benzylamide, N-acetyldehydro-3-(2-thienyl)alanine N'-methylamide, N-acetyldehydro-3-(2-thienyl)alanine morpholide, N-acetyldehydro-3-(2-thienyl)alanine, N-cinnamoyldehydrophenylalanyl-L-tyrosine, N-benzoyldehydroisoleucyl-L-tyrosine, N-cinnamoyldehydrophenyl-alanine, N'-methylamide, N-cinnamoyldehydrophenylalanine 1,1-dimethyl-2-propinylamide, N-cinnamoyldehydrophenylalanine morpholide, N-benzoyl-3-methyl-3-cinnamenyldehydroalanyl-L-tyrosine, N-benzoyl-3-methylphenyldehydroalanyl-L-leucine, N-acetyldehydro-3-(2-thienyl)alanine N'-methylamide, and N-acetyldehydro-3-(2-thienyl)alanine N'-1,1-dimethyl-2-propinylamide.

Additional examples of compounds according to the invention which may be mentioned are: N-crotonoyldehydro-3-(2-thienyl)-alanine, -alanine methyl ester, -alanaine thioethyl ester and alanine thiomethyl ester, N-ethoxyacetyldehydro-3-(2-thienyl)alanine methyl ester, N-acetyldehydrophenylalanyl-3-(5-methylthienyl-2)dehydroalanine, N-benzoyldehydrophenylalanine methyl ester, N-benzoyldehydrophenylalanine thioethyl ester, N-acetyldehydrophenylalanine thioethyl ester, N-acetyldehydrophenylalanine thiomethyl ester, N-acetyldehydro-3-(2-thienyl)alanine thiomethyl ester, N-acetyldehydro-3-(2-thienyl)alanine 2-carboxythioethyl ester, N-acetyldehydro-3-(2-thienyl)alanine thioethyl ester, N-acetyldehydro-3-(2-thienyl)alanine 4-chlorothiophenyl ester, N-(3-trifluoromethylbenzoyl)-dehydro-3-(2-thienyl)alanine thioethyl ester, N-acetyldehydrophenylalanine-3-(3-chlorophenyl)dehydroalanine thiomethyl ester, N-cinnamoyldehydrophenylalanine thiomethyl ester, N-(3-trifluoromethylbenzoyl)-3-(2-thienyl)alanine methyl ester, N-crotonyldehydro-3-(2-thienyl)alanine, N-acetyldehydro-3-(2-thienyl)alanyldehydro-3-(2-thienyl)alanine, N-benzoyl-dehydro-3-(2-thienyl)alanine, N-(3-trifluoromethylbenzoyl)dehydro-3-(2-thienyl)alanine, N-acetyldehydro-3-(2-thienyl)alanyldehydro-3-(4-nitrophenyl)alanine, N-benzoyldehydrophenyl-alanine, N-acetyldehydro-3-(2-thienyl)alanyl-N-methylglycine, N-(3,4,5-trimethoxycinnamoyl)dehydro-3-(2-thienyl)alanyl-L-tyrosine, N-crotonoyldehydro-3-(2-thienyl)alanyl-L-tyrosine, N-acetyldehydro-3-(5-nitro-2-thienyl)alanyl-L-tyrosine, N-(2-thenoyl)dehydro-3-(2-thienyl)alanyl-L-tyrosine, N-crotonoyl-dehydro-3-(2-thienyl)alanyl-L-leucine, N-acetyldehydro-3-(2-thienyl)alanyl-O-methyl-L-tyrosine, N-acetyldehydro-3-(2-thienyl)alanyl-L-tryptophan, N-acetyldehydro-3-(2-thienyl alanyl-L-glycine, N-acetyldehydro-3-(2-thienyl)alanyl-2-(4-hydroxyphenyl)-D-glycine, N-benzoyldehydrophenylalanyl-L-leucyglycine 4-methoxyphenylamide, N-acetyldehydro-3-(2-thienyl)alanyl-2-(1,4-cyclohexanedien- 1-yl)-D-glycine, N-acetyldehydro-3-(2-thienyl)alanyl-L-glutamic acid, N-acetyldehydro-3-(2-thienyl)alanyl-L-leucine, N-acetyldehydro-3-(2-thienyl)alanyl-L-phenylalanine, N-acetyldehydro-3-(2-thienyl)alanyl-L-β-alanine, N-benzoyldehydrophenylalanylglycine, N-acetyldehydro-3-(2-thienyl)-alanyl-DL-valine, N-(2-thenoyl) dehydro-3-(2-thienyl)alanyl-2-(1,4-cyclohexanedien-1-yl)-D-glycine, N-acetyldehydro-3-(2-thienyl)alanyl-L-threonine, N-acetyldehydro-3-(2-thienyl)alanyl-L-aspartic acid, N-benzoylde-hydrophenylalanine-L-tryptophan, N-(3-trifluoromethylbenzoyl)dehydro-3-(2-thienyl)alanyl-L-leucine, N-(3-trifluoromethylbenzoyl)-dehydro-3-(2-thienyl)alanyl-L-phenylalanine, N-(3-trifluoromethylbenzoyl)dehydro-3-(2-thienyl)alanylglycine, N-acetyldehydro-3-(2-thienyl)alanyl-3-(2-thienyl)-dehydroalanyl-L-tyrosine tert.-butyl ester, N-acetyldehydro-3-(2-thienyl)alanyl-3-(2-thienyl)dehydroalanyl-L-tyrosine benzyl ester, N-acetyldehydro-3-(2-thienyl)alanyl-3-(2-thienyl)dehydroalanyl-L-tyrosine methyl ester, N-acetyldehydro-3-(2-thienyl)alanyl-N-methyl-L-tyrosine methyl ester, N-acetyldehydro-3-(2-thienyl)alanyl-N-methyl-L-tyrosine, N-acetyldehydro-3-(3-nitro-4-hydroxyphenyl)alanyl-L-tyrosine tert.-butyl ester, N-acetyldehydro-3-(3-nitro-4-hydroxyphenyl)alanyl-L-tyrosine, N-benzoyldehydro-3-(4-pyridyl)alanyl-L-tyrosine methyl ester, N-benzoyldehydro-3-(4-pyridyl)alanyl-L-tyrosine, N-(4-nitrophenyl)acetyldehydro-3-(2-thienyl)alanyl-L-tyrosine, N-(4-nitrophenyl)acetyldehydro-3-(2-thienyl)alanyl-L-tyrosine methyl ester, N-acetyldehydro-3-(2-thienyl)alanyl-3-(2-thienyl)dehydroalanyl-L-tyrosine tert.-butyl ester, N-acetyldehydro-3-(2-thienyl)alanyl-3-(2-thienyl)dehydroalanyl-L-tyrosine, N-benzoyldehydroisoleucyl-L-tyrosine methyl ester, N-(2-thienyl)-acetyldehydro-3-(2-thienyl)alanyl-L-tyrosine, N-(2-thienyl)-acetyldehydro-3-(2-thienyl)alanyl-L-tyrosine tert.-butyl ester, N-(2-thienyl)acetyldehydro-3-(2-thienyl)alanyl-L-tyrosine benzyl ester, N-(2-thienyl)acetyldehydro-3-(2-thienyl)alanyl-L-tyrosine methyl ester, N-benzoyldehydrophenylalanyl-L-leucylglycine amide, N-benzoyldehydrophenylalanyl-L-propyl-L-leucylglycine amide, N-acetyldehydro-3-(2-thienyl)alanyl-2-methylalanine methyl ester, N-acetyldehydro-3-(2-thienyl)alanyl-2-methylalanine, the salt of N-acetyldehydro-3-(2-thienyl)alanine with methylamine, with 1,1-dimethylpropargylamine and with lithium, the salt of N-acetyldehydro-3-(2-thienyl)alanyl-L-tyrosine with morpholine, with piperidine, with ethylenediamine, with triethanolamine, with DL-canavanine, with L-arginine and L-lysine, N-acetyldehydro-3-(2-thienyl)alanyl-L-tyrosine 2O-dimethylaminopropylamide, N-acetyldehydro-3-(2-thienyl)alanyl-L-tyrosine amide, N-acetyldehydro-3-(2-thienyl)alanyl-L-tyrosine methylamide, N-acetyldehydro-3-(2-thienyl)alanyl-L-tyrosine hydrazide, N-benzoyldehydro-3-(2-thienyl)alanyl-L-tyrosine 6-aminohexaneamide, N-benzoyldehydro-3-(2-thienyl)alanyl-L-tyrosine 4-aminobutane-amide, N-benzoyl-dehydro-3-(2-thienyl)alanyl-L-tyrosine hydrazide, N-ethoxyacetyldehydro-3-(2-thienyl)alanine 4-methylpiperazide, N-ethoxyacetyldehydro-3-(2-thienyl)alanine anilide, N-ethoxyacetyldehydro-3-(2-thienyl)alanine cyclohexylamide, N-ethoxyacetyldehydro-3-(2-thienyl)alanine amide, N-crotonyldehydro-3-(2-thienyl)alanine 4-methylpiperazide, N-crotonoyldehydro-3-(2-thienyl)alanine 3-dimethylaminopropylamide, N-crotonoyldehydro-3-(2-thienyl)alanine 6-aminohexane-amide, N-crotonoyldehydro-3-(2-thienyl)alanine 4-hydroxyanilide, N-acetyldehydrophenylalanyl-3-(2-thienyl)-dehydroalanine methylamide, N-(3-trifluoromethylbenzoyl)dehydro-3-(2-thienyl)alanine anilide, N-(3-trifluoromethylbenzoyl)dehydro-3-(2-thienyl)alanine 4-methylpiperazide, N-(3-trifluoromethylbenzoyl)-dehydro-3-(2-thienyl)alanine 2-dimethylaminopropylamide, N-(3-trifluoromethylbenzoyl)dehydro-3-(2-thienyl)alanine amide, N-acetyldehydro-3-(2-thienyl)alanyl-3-methyl-3-(thienyl)dehydroalanine hexylamide, N-nicotinoyl-3-(2-thienyl)dehydroalanine propargylamide, N-(2-thienylacetyl)dehydro-3-(2-thienyl)-alanine 3-dimethylaminopropylamide, N-benzoyldehydro-3-(2-thienyl)alanine 3-dimethylaminopropylamide, N-benzoyldehydro-3-(2-thienyl)alanine anilide, N-benzoyldehydro-3-(2-thienyl)alanine methylamide, N-benzoyldehydro-3-(2-thienyl)alanine hexylamide, N-benzoyldehydro-3-(2-thienyl)alanine propargylamide, N-benzoylhydro-3-(2-thienyl)alanine hydrazide, N-benzoyldehydrophenylalanine anilide, methylamide, 1,1-dimethylpropargylamide, hexylamide, cyclohexylamide, morpholide, 4-methoxyphenylhydrazide, 2-phenylcyclopropylamide, 3,4,5-trimethoxyanilide, 3-dimethylaminopropylamide and propargylamide, N-acetyldehydro-3-(2-thienyl)alanine 2-(4-imidazolyl)ethylamide, hexylamide, 2-phenylcyclopropylamide, benzylamide, 3-dimethylaminopropylamide, piperidide, 4-methylpiperazide, 4-pheylpiperazide, 4-(2-hydroxyethyl)piperazide, amide, 2,2-dimethylhydrazide, anilide, 4-methylcyclohexylamide, 3-morpholinopropylamide, 1-phenylethylamide, 3-carboxypropylamide, hydrazide, 2-sulphonic acid ethylamide, 1-ethinylcyclohexylamide, benzyloxyamide, 2-hydroxyethylamide, esterified with phosphoric acid, and morpholide, N-acetyldehydro-3-(2-thienyl)alanine propargylamide, N-acetyldehydro-3-(2-thienyl)alanine 3,4,5-trimethoxyanilide and N-acetyldehydro-3-(2-thienyl)alanine-2-(benzothiazol-2-yl)hydrazide.

The compounds can exist both in the form of a racemate and in the form of isolated optical isomers having a definite absolute configuration. In addition, cis/trans isomers can occur in the synthesis, for example, of N-benzoyldehydrophenylalanyl-L-leucine methyl ester. In some cases, for example, in the case of N-acetyldehydro-3-(2-thienyl)alanyl-L-tyrosine, only one of the isomers is preferentially formed, as could be demonstrated by 13-NMR spectroscopy.

The active compounds according to the invention have a histolytic action, which depends on the dose which is given, preferably by local administration. By local administration there are to be understood herein as being included the following types of administration: subcutaneous and intracutaneous, administration.

Necroses usually occur in the immediate region of the point of administration, but occasionally also at a distance therefrom (lymphogenic). If the necrotic region breaks open, it is free from putrid material even for a relatively long period, although in the case of experimental animals feed, faeces, sawdust and other material come into contact with the open wound.

The activity of the third component of the immunohaemolytic complement system is considerably decreased.

The necrotic tissue is sharply divided from the surrounding healthy tissue; it appears macroscopically and miscroscopically as if it were "stamped out".

The general behaviour of the experimental animals is not influenced by the size of the necrosis. There is no poisoning of the entire organism.

In the acute test for intraveneous injection in rats, the $LD_{50}$ of the compounds according to the invention is in the order of size of 300 mg/kg.

A daily injection of 80 mg/kg in rabbits over a period of 27 days was tolerated completely without reaction.

As has been mentioned above, the present invention also includes the use of the active compounds according to the invention, for the treatment of those tissues in the field of medicine which prevent and interfere with the course of normal biological functions.

Such tissues are, for example:

In addition, the compounds according to the invention can be used for fibrotic tissues of every type, in particular for the treatment of keloids, Ulcera crura, burn ulcers, decubital ulcers as well as clavi and onychomycoses and scar tissue and for the therapy and prophylaxis of emboli and thromboses.

The compounds according to the invention can also be used for resolving moles, atheromas and lipomas and for removing deep abscesses which, under certain circumstances, are fistulous.

The compounds according to the invention can additionally be used for the regeneration of cavernomas and tuberculomas.

The compounds according to the invention can also be used for the scar-free regeneration of tissue defects in the case of leprosy and other skin, mucous membrane and epithelium defects of various origins, above all those which are caused by infections by bacteria, fungi and pathogens of tropical diseases, such as, for example, those of leichmaniasis, framboesia, pinta and the like.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

"Medicament" as used in this specification means physically discrete coherent portions suitable for medical administration. "Medicament in dosage unit form" as used in this specification means physically discrete coherent units suitable for medical administration each containing daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic. Preferred injection solutions are those having a pH of from 7.0 to 9.5, most preferably from 8 to 9. The compounds of the invention which are free acids may be conveniently dissolved in dilute physiologically acceptable bases and then brought to the required pH by the addition of a dilute physiologically acceptable acid.

Examples of physiologically acceptable bases which may be mentioned are inorganic hydroxides, carbonates and bicarbonates, in particular those of sodium and potassium. Examples of physiologically acceptable acids which may be mentioned are organic acids, such as citric acid, oxalic acid, lactic acid, benzoic acid, salicyclic acid and acetic acid, or also inorganic acids, such as, for example, dilute hydrochloric or sulphuric acid.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain colouring agents and preservatives.

The pharmaceutical compositions according to the invention generally contain from 1 to 90, usually from 5 to 50% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: ampoules. Some of these forms may be made up for delayed release of the active ingredient. Some, such as ampoules, include a protective envelope which renders the portions of the medicament physically discrete and coherent.

The preferred daily dose for administration of the medicaments of the invention is from 50 mg to 5 g of active ingredient most preferably from 100 mg to 2 g of active ingredient.

The production of the above mentioned pharmaceutical compositions and medicaments is carried out by any method known in the art, for example, by mixing the active ingredient(s) with the diluent(s) to form a pharmaceutical composition (e.g. a solution or suspension) and then forming the composition into the medicament (e.g. ampoules of injection solution or suspension).

This invention further provides a method of combating the above mentioned diseases in warm-blooded animals, which comprises administering to the animals a compound of the invention alone or in admixture with a diluent or in the form of a medicament according to the invention.

It is envisaged that these active compounds will be administered parenterally (for example intramuscularly, intracutaneously or subcutaneously, topically, preferably intracutaneously or subcutaneously. Preferred pharmaceutical compositions and medicaments are therefore those adapted for local administration, such as injection solutions and suspensions, ointments, gels, lotions and creams. Administration in the method of the invention is preferably subcutaneous, intracutaneous intratumoral and peritumoral.

In general, it has proved advantageous to administer amounts of from 1 mg to 100 mg preferably from 2 to 40 mg, per kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, whilst other cases the upper limit mentioned must be exceeded to achieve the desired results. Where larger amounts are administered it can be advisable to divide these into several individual administrations over the course of the day.

In the examples given below, the optical rotation was measured at c=2 in dimethylformamide.

The metling points were determined in a Tottoli apparatus and are uncorrected.

EXAMPLE 1

N-Benzoyldehydro-$\beta$-(2-thienyl)alanine methyl ester 2 g of 2-phenyl-4-(2-thenylidene)-5(4H)-oxazolone are dissolved in 50 ml of absolute methanol and the solution is kept at room temperature for 16 hours. The reaction solution is then evaporated, the residue is taken up in glacial acetic acid/ethylene chloride, the mixture is filtered and the product is crystallised by concentrating the filtrate. 2 g (88.8% of theory) of N-benzoyldehydro-$\beta$-(2-thienyl)alanine methyl ester of melting point 162° C. are obtained.

$C_{15}H_{13}NO_3S$: calculated: C 62.70%; H 4.56%; N 4.87%; S 11.16%; found: C 62.81%; H 4.67%; N 4.85%; S 11.18%.

EXAMPLE 2

N-Acetyldehydro-$\beta$-(2-thienyl)alanine ethyl ester is obtained from 2-methyl-4-(2-thenylidene)-5(4H)-oxazolone and absolute ethanol analogously to Example 1; melting point 109°–110° C.

Yield 82%.

$C_{11}H_{13}NO_3S \cdot H_2O$; calculated: C 51.42%; H 5.8%; N 5.4%; S 12.5%; found: C 41.80%; H 6.0%; N 5.4%; S 12.7%.

EXAMPLE 3

N-Acetyldehydrophenylalanine is obtained by saponifying 2-methyl-4-benzylidene-5(4H)-oxazolone (preparation in the literature: Beilstein X, page 683); melting point 188°–190° C.

EXAMPLE 4

N-Crotonoyldehydro-3-(2-thienyl)alanine methyl ester is obtained from 2-(1-propenyl)-4-(2-thenylidene)-5(4H)-oxazolone and methanol analogously to Example 1.

Melting point: 174°–176° C.; yield: 54% of theory.

$C_{12}H_{13}NO_3S$; calculated: C 57.35%; H 5.21%; N 5.57%; S 12.76%. found: C 57.45%; H 5.31%; N 5.68%; S 12.55%.

EXAMPLE 5

N-Crotonoyldehydro-3-(2-thienyl)alanine thioethyl ester is obtained from 2-(1-propenyl)-4-(2-thenylidene)-5(4H)-oxazolone and ethylmercaptan analogously to Example 1.

Melting point: 176° C.; yield: 80% of theory.

$C_{13}H_{15}NO_2S_2$; calculated: C 55.49%; H 5.33%; N 4.98%; S 22.79%; found: C 55.61%; H 5.44%; N 4.93%; S 22.96%.

EXAMPLE 6

N-Crotonoyldehydro-3-(2-thienyl)alanine thiomethyl ester is obtained from 2-(1-propenyl)-4-(2-thenylidene)-5(4H)-oxazolone and methylmercaptan analogously to Example 1.

Melting point: 178°–180° C.; yield: 63% of theory.

$C_{12}H_{13}NO_2S_2$; calculated: C 53.91%; H 4.90%; N 5.24%; S 23.99%; found: C52.52%; H 4.91%; N 5.25%; S 24.21%.

EXAMPLE 7

N-Ethoxyacetyldehydro-3-(2-thienyl)alanine methyl ester is obtained from 2-ethoxymethyl-4-(2-thenylidene)-5(4H)-oxazolone and methanol analogously to Example 1.

EXAMPLE 8

N-Benzoyldehydrophenylalanine methyl ester is obtained from 2-phenyl-4-benzylidene-5(4H)-oxazolone and methanol analogously to Example 1.

Melting point: 141°–142° C.; yield: 65% of theory.

$C_{17}H_{15}NO_3$; calculated: C 72.6%; H 5.3%; N 5.0%; found: C 72.7%; H 5.3%; N 4.9%.

EXAMPLE 9

N-Acetyldehydrophenylalanine thioethyl ester is obtained from 2-methyl-4-benzylidene-5(4H)oxazolone and ethylmercaptan analogously to Example 1 (in an autoclave for one week at 50° C.).

Melting point: 106°–107° C.; yield: 7% of theory.

$C_{13}H_{15}NO_2S$; calculated: C 62.62%; H 6.06%; N 5.62%; S 12.86%; found: C 62.89%; H 6.03%; N 5.65%; S 12.96%.

EXAMPLE 10

N-Acetyldehydrophenylalanine thiomethyl ester is obtained from 2-methyl-4-benzylidene-5(4H)oxazolone and methylmercaptan, in an autoclave for one week at 50° C., analogously to Example 1.

Melting point: 157°–158° C.; yield: 51% of theory.

$C_{12}H_{13}NO_2S$; calculated: C 61.25%; H 5.57%; N 5.95%; S 13.63%; found: C 61.31%: H 5.62%: N 5.91%: S 13.51%.

EXAMPLE 11

N-Acetyldehydro-3-(2-thienyl)alanine thiomethyl ester is obtained from 2-methyl-4-(2-thenylidene)-5(4H)oxazolone and methylmercaptan, in an autoclave at 70° C., analogously to Example 1.

Melting point: 144°–145° C.; yield: 45% of the theory.

$C_{10}H_{11}NO_2S_2$; calculated: C 49.77%; H 4.59%; N 5.80%; S 26.57%; found: C 49.61%; H 4.68%; N 5.75%; S 26.41%.

EXAMPLE 12

N-Acetyldehydro-3-(2-thienyl)alanine 3-carboxythioethyl ester is obtained from 2-methyl-4-(2-thenylidene)-5(4H)oxazolone and 3-mercaptopropionic acid, in an autoclave, analogously to Example 1.

Melting point: 172°–174° C.; yield: 66.9% of theory.

$C_{12}H_{13}NO_4S_2$; calculated: C 48.14%; H 4.38%; N 4.68%; S 21.42%; found: C 48.28%; H 4.40%; N 4.71%; S 21.44%.

EXAMPLE 13

N-Acetyldehydro-3-(2-thienyl)alanine thioethyl ester is obtained from 2-methyl-4-(2-thenylidene)-5(4H)oxazolone and ethylmercaptan analogously to Example 1.

Melting point: 110°–112° C.; yield: 98% of theory $C_{11}H_{13}NO_2S_2$; calculated: C 51.74%; H 5.13%; N 5.49%; S 25.11%; found: C 51.84%; H 5.12%; N 5.57%; S 24.97%.

EXAMPLE 14

N-Acetyldehydro-3-(2-thienyl)alanine 4-chlorothiophenyl ester is obtained from 2-methyl-4-(2-thenylidene)-5(4H)oxazolone and 4-chlorophenylmercaptan, in the presence of triethylamine, analogously to Example 1.

Melting point: 177°–179° C.; yield: 48.8% of theory.

$C_{15}H_{12}ClNO_2S_2$; calculated: C 53.33%; H 3.58%; Cl 10.49%; N 4.15%; S 18.98%; found: C 53.45%; H 3.57%; Cl 10.63%; N 4.13%; S 19.10%.

EXAMPLE 15

N-(3-Trifluoromethylbenzoyl)dehydro-3-(2-thienyl)alanine thioethyl ester is obtained from 2-(3-trifluoromethylphenyl)-4-(2-thenylidene)-5(4H)oxazolone and ethylmercaptan, in the presence of NaH, analogously to Example 1.

Melting point: 139°–140° C.; yield: 50% of theory.

$C_{17}H_{14}F_3NO_2S_2$; calculated: C 52.98%; H 3.66%; F 14.79%; N 3.63%; S 16.64%; found: C 53.18%; H 3.60%; F 14.9%; N 3.50%; S 16.63%.

EXAMPLE 16

N-Benzoyldehydrophenylalanine thioethyl ester is obtained from 2-phenyl-4-benzylidene-5(4H)oxazolone and ethylmercaptan analogously to Example 1.

Melting point: 150° C. (decomposition); yield: 47% of theory.

$C_{18}N_{17}NO_2S$; calculated: C 69.43%; H 5.50%; N 4.50%; S 10.30%; found: C 69.27%; H 5.55%; N 4.54%; S 10.32%.

EXAMPLE 17

N-Acetyldehydrophenylalanine-3-(3-chlorophenyl)-dehydroalanine thiomethyl ester is obtained from 4-(3-chlorobenzylidene)-2-(1-acetamido-2-phenylvinyl)-5(4H)oxazolone and methylmercaptan, in a pressure flask for one week, analogously to Example 1.

Melting point: 166°–167° C.; yield: 38.8% of theory.

$C_{21}H_{19}ClN_2O_3S$; calculated: C 60.79%; H 4.61%; Cl 8.54%; N 6.75%; S 7.73%; found: C 60.74%; H 4.48%; Cl 8.58%; N 6.82%; S 7.80%.

EXAMPLE 18

N-Cinnamoyldehydrophenylalanine thiomethyl ester is obtained from 2-(2-phenylvinyl)-4-benzylidene-5(4H)oxazolone and methylmercaptan, in an autoclave for one week, analogously to Example 1.

Melting point: 182°–183° C.; yield 28.5% of theory.

$C_{19}H_{17}NO_2S$; calculated: C 70.56%; H 5.30%; N 4.33%; S 9.91%; found: C 70.40%; H 5.39%; N 4.41%; S 9.61%.

EXAMPLE 19

N-(3-Trifluoromethylbenzoyl)-3-(2-thienyl)alanine methyl ester is obtained from 2-(3-trifluoromethylphenyl)-4-(2-thenylidene)-5(4H)oxazolone and methanol, in the presence of sodium hydride, analogously to Example 1.

Melting point: 117°–118° C.; yield: 64.8% of theory.

$C_{16}H_{12}F_3NO_3S$; calculated: C 54.08%; H 3.04%; F 16.04%; S 9.03%; found: C 54.01%; H 3.47%; F 15.90%; S 9.05%.

EXAMPLE 20

N-Phenylacetyldehydro-β-(thienyl)alanine is obtained by saponifying 2-benzyl-4-(2-thenylidene)-5(4H)-oxazolone; melting point 193°–195° C.; yield: 8.2% of theory.

$C_{15}H_{13}NO_3S$; calculated: C 62.70%; H 4.56%; N 4.88%; S 11.16%; found: C 62.68%; H 4.55%; N 4.96%; S 11.26%.

EXAMPLE 21

DL-N-Acetylphenylalanyldehydro-(3-chlorophenyl)alanine 1.8 g (0.005 mol) of 2-(1-acetamido-2-phenylethyl)-4-(3-chlorobenzylidene)-5(4H)-oxazolone are suspended in 7 ml of acetone, and 7.5 ml of 2 N NaOH are added.

After stirring for half an hour, the reaction solution is acidified to pH 3 with citric acid and the precipitate which separates out if filtered off and washed until neutral.

Melting point: 195°–196° C.; yield: 1.6 g (84.2% of theory).

$C_{20}H_{19}ClN_2O_4$; calculated: C 62.10%; H 4.95%; Cl 9.17%; N 7.24%; found: C 62.31%; H 4.77%; Cl 9.03%; N 7.31%.

EXAMPLE 22

L-N-tert.-Butoxycarbonylphenylalanyldehydro-(3-chlorophenyl)alanine is obtained from 2-(1-tert.-butoxycarbonylamido-2-phenylethyl)-4-(3-chlorophenyl)-5-(4H)-oxazolone analogously to Example 21, with recrystallisation from aqueous acetone. Melting point: 173° C. (decomposition), $[\alpha]_D^{20}+78.6°$ (c=1; dimethylformamide), yield: 83.3% of theory.

$C_{23}H_{25}ClN_2O_5$; calculated: C 62.09%; H 5.66%; Cl 7.97%; N 6.30%; found: C 62.26%; H 5.66%; Cl 7.95%; N 6.44%.

EXAMPLE 23

L-Phenylalanyldehydro-(3-chlorophenyl)alanine is obtained from 2.5 g of the above compound by dissolving in 15 ml of anhydrous trifluoroacetic acid, allowing the mixture to stand at room temperature for one hour, evaporating, taking up the residue in water, adjusting the pH of the solution to 8 with NH$_3$ and evaporating the solution until crystallisation starts.

Melting point: 235°–236° C.; $[\alpha]_D^{20}-31.5°$ (c=1; dimethylformamide); yield: 1.7 g (89.5% of theory).

$C_{18}H_{17}ClN_2O_3$; calculated: C 62.70%; H 4.97%; Cl 10.28%; N 8.13%; found: C 62.55%; H 5.35%; Cl 10.15%; N 8.19%.

EXAMPLE 24

N-Acetyldehydro-3-(2-thienyl)alanine is obtained from 4-thenylidene-2-methyl-5(4H)oxazolone analogously to Example 21.

Melting point: 222°–223° C.; yield: 5.7% of theory.

$C_9H_9NO_3S$; calculated: C 51.17%; H 4.30%; N 6.63%; S 15.18%; found: C 51.21%; H 4.37%; N 6.65%; S 15.32%.

EXAMPLE 25

N-Acetyldehydrophenylalanyl-3-(5-methylthienyl-2)dehydroalanine is obtained from 4-(5-methylthenylidene)-2-(1-acetamido-2-phenylvinyl)-5(4H)-oxazolone analogously to Example 21.

Melting point: 193°–194° C.; yield: 40% of theory.

$C_{19}H_{18}N_2O_4S$; calculated: C 61.61%; H 4.90%; N 7.56%; S 8.66%; found: C 61.54%; H 4.96%; N 7.55%; S 8.70%.

EXAMPLE 26

N-Crotonoyldehydro-3-(3-thienyl)alanine is obtained from 2-(1-propenyl)-4-(2-thenylidene)-5(4H)-oxazolone analogously to Example 21.

Melting point: 226° C.; yield: 88% of theory.

$C_{11}H_{11}NO_3S$; calculated: C 55.68%; H 4.67%; N 5.90%; S 13.51%; found: C 55.23%; H 4.71%; N 6.03%; S 13.96%.

EXAMPLE 27

N-Acetyldehydro-3-(2-thienyl)alanyldehydro-3-(2-thienyl)alanine is obtained from 2-[1-acetamido-2(2-thienyl)vinyl]-4-(2-thenylidene)-5(4H)oxazolone analogously to Example 21.

Melting point: 218° C.; yield: 80% of theory.

$C_{16}H_{14}N_2O_4S_2$; calculated: C 53.02%; H 3.89%; N 7.73%; S 17.69%; found: C 52.99%; H 3.94%; N 7.96%; S 17.70%.

EXAMPLE 28

N-Benzoyldehydro-3-(2-thienyl)alanine is obtained from 2-phenyl-5-(2-thenylidene)-5(4H)oxazolone analogously to Example 21.

Melting point: 235° C.; yield: 94% of theory.

$C_{14}H_{11}NO_3S$; calculated: C 61.52%; H 4.06%; N 5.12%; S 11.74%; found: C 61.50%; H 4.08%; N 5.14%; S 11.70%.

EXAMPLE 29

N-(3-Trifluoromethylbenzoyl)dehydro-3-(2-thienyl)alanine is obtained from 4-thenylidene-2-(3-trifluoromethylphenyl)-5(4H)oxazolone analogously to Example 21.

Melting point: 200°–202° C.; yield: 93% of theory.

$C_{15}H_{10}F_3NO_3S$; calculated: C 52.76%; H 2.96%; F 16.70%; N 4.10%; S 9.39%; found: C 52.89%; H 2.92%; F 16.60%; N 4.18%; S 9.36%.

EXAMPLE 30

N-Acetyldehydro-3-(2-thienyl)alanyldehydro-3-(4-nitrophenyl)alanine is obtained from 4-(4-nitrobenzylidene)-2-[1-acetamido-2-(2-thienyl)vinyl]-5(4H)oxazolone analogously to Example 21.

Melting point: 196°–197° C.; yield: 55.7% of theory.

$C_{18}H_{15}N_3O_6S$; calculated: C 53.86%; H 3.77%; N 10.47%; S 7.99%; found: C 53.80%; H 3.81%; N 10.52%; S 7.85%.

EXAMPLE 31

N-Benzoyldehydrophenylalanine is obtained from 4-benzylidene-2-phenyl-5(4H)oxazolone analogously to Example 21.

Melting point: 25° C.; yield: 88% of theory.

$C_{16}H_{13}NO_3$; calculated: C 71.90%; H 4.90%; N 5.24%; found: C 71.98%; H 4.80%; N 5.25%.

The examples which follow were formed accoring to the following general instructions:

0.025 mol of the aminoacid to be subjected to condensation is suspended in 10 ml of acetone, 25 ml of 1 N NaOH are added whilst stirring and the solution formed is mixed with a suspension of the appropriately substituted 5(4H)-oxazolone in acetone. The mixture is stirred at room temperature for ½ to 20 hours, depending on the reactivity of the aminoacid. 25 ml of 1 n HCl are then added to the filtered reaction solution and the acetone is distilled off in vacuo. The desired end product crystallises out of the aqueous phase and is recrystallised from aqueous alcohol.

EXAMPLE 32

N-Acetyldehydrophenylalanyl-L-proline is obtained from 2-methyl-4-phenyl-5(4H)-oxazolone and L-proline.

Melting point: 152°-155° C.; $[\alpha]_D^{20} + 69.5°$; yield: 59% of theory.

$C_{16}H_{18}N_2O_4 \cdot \frac{1}{2}H_2O$; calculated: C 61.72%; H 6.15%; N 9.00%; found: C 62.15%; H 6.43%; N 8.96%.

EXAMPLE 33

N-Acetyldehydrophenylalanyl-D-proline

Melting point: 151°-253° C.; $[\alpha]_D^{20} - 69.6°$; yield: 55% of theory.

$C_{16}H_{18}N_2O_4$; calculated: C 61.72%; H 6.15%; N 9.0%; found: C 61.75%; H 6.30%; N 8.94%.

EXAMPLE 34

N-Acetyldehydrophenylalanyl-D-tryosine

Melting point: 210° C.; $[\alpha]_D^{20} - 43.4°$ (c=2; pyridine); yield: 61.3% of theory.

$C_{20}H_{20}N_2O_5$; calculated: C 65.21%; H 5.47%; N 7.60%; found: C 64.56%; H 5.86%; N 7.77%.

EXAMPLE 35

N-Acetyldehydrophenylalanyl-L-leucine

Melting point: 206°-207° C.; $[\alpha]_D^{20} - 22.5°$; yield: 65.7% of theory.

$C_{17}H_{22}N_2O_4$; calculated: C 64.13%; H 6.97%; N 8.80%; found: C 64.26%; H 7.31%; N 8.78%.

EXAMPLE 36

N-Acetyldehydrophenylalanyl-L-methionine

Melting point: 91°-93° C., $[\alpha]_D^{20} - 74.4°$; yield: 70% of theory.

$C_{16}H_{20}N_2O_4S$; calculated: C 57.12%; H 5.99%; N 8.33%; S 9.53%; found: C 57.02%; H 6.03%; N 8.40%; S 9.46%.

EXAMPLE 37

N-Acetyldehydrophenylalanyl-L-aspartic acid

Melting point: 182°-184° C.; $[\alpha]_D^{20} - 46.65°$; yield: 63.5% of theory.

$C_{15}H_{16}N_2O_6 \cdot H_2O$; calculated: C 53.25%; H 5.36%; N 8.28%; found: C 53.48%; H 4.92%; N 8.32%.

EXAMPLE 38

N-Acetyldehydrophenylalanyl-L-glutamine

Melting point: 188° C; $[\alpha]_D^{20} - 74.5°$; yield: 54% of theory.

$C_{16}H_{19}N_3O_5$; calculated: C 57.65%; H 5.75%; N 12.61%; found: C 58.17%; H 5.79% N 13.16%.

EXAMPLE 39

N-Acetyldehydrophenylalanyl-DL-3-fluoroalanine

Melting point: 180° C. (decomposition); yield: 58.7% of theory.

$C_{14}H_{15}FN_2O_4$; calculated: C 57.14%; H 5.14%; F 6.46%; N 9.52%; found: C 57.22%; H 5.22%; F 6.30%; N 9.58%.

EXAMPLE 40

N-Acetyldehydrophenylalanyl-L-serine

Melting point: 179° C. (decomposition); $[\alpha]_D^{20} + 1.15°$; yield: 48.5% of theory.

$C_{14}H_{16}N_2O_5$; calculated: C 57.35%; H 5.52%; N 9.58%; found: C 57.48%; H 5.47%; N 9.66%.

EXAMPLE 41

N-Acetyldehydrophenylalanyl-L-tyrosine

Melting pint: 219°-220° C.; preparation in the literature.

EXAMPLE 42

N-Acetyldehydrophenylalanylglycine

Melting point: 191°-192° C.; preparation in the literature.

EXAMPLE 43

N-Acetyldehydrophenylalanyl-L-(p-nitrophenyl)alanine

Melting point: 192°-193° C. (from ethanol/petroleum ether/isopropyl ether); $[\alpha]_D^{20} - 110.7°$; yield: 70.3% of theory.

$C_{20}H_{19}N_3O_6$; calculated: C 60.45%; H 4.82%; N 10.58%; found: C 60.40%; H 4.90%; N 10.43%.

EXAMPLE 44

N-Acetyldehydroalanyl-DL-(p-chlorophenyl)alanine

Melting point: 214°-215° C. (from ether/petroleum ether); yield: 66.9% of theory.

$C_{20}H_{19}ClN_2O_4$; calculated: C 62.10%; H 4.95%; Cl 9.17%; N 7.24%; found: C 62.39%; H 5.02%; Cl 9.14%; N 7.11%.

EXAMPLE 45

N-Acetyldehydro(p-methylphenyl)alanyl-L-tyrosine

Melting point: 220°-221° C.; $[\alpha]_D^{20} - 38.5°$; yield: 47.6% of theory.

$C_{21}H_{22}N_2O_5$; calculated: C 65.95%; H 5.80%; N 7.33%; found: C 65.96%; H 5.80%; N 7.16%.

EXAMPLE 46

N-Benzoyl-2-cyclohexylideneglycyl-L-tyrosine

Melting point: 121° C.; $[\alpha]_D^{20} - 0.5°$; yield: 75.8% of theory.

$C_{24}H_{26}N_2O_5$; calculated: C 68.23%; H 6.20%; N 6.63%; found: C 68.16%; H 6.18%; N 6.65%.

EXAMPLE 47

N-Benzoyl-2-(2-cyclohexenylidene)glycyl-L-tyrosine

Melting point: 126° C.; $[\alpha]_D^{20} -5.7°$; yield: 60% of theory.

$C_{24}H_{24}N_2O_5$; calculated: C 68.56%; H 5.75%; N 6.66%; found: C 68.46%; H 5.70%; N 6.56%.

EXAMPLE 48

N-Acetyldehydro-3-(2-furyl)alanyl-L-tyrosine

Melting point: 217° C. (ethanol/petroleum ether); $[\alpha]_D^{20} -29.1°$; yield: 31% of theory.

$C_{18}H_{18}N_2O_6$; calculated: C 60.33%; H 5.06%; N 7.82%; found: C 60.37%; H 5.11%; N 7.70%.

EXAMPLE 49

N-Acetyldehydro-3-cinnamenylalanyl-L-tyrosine

Melting point: 220°-221° C.; $[\alpha]_D^{20} -44.2°$; yield: 57.3% of theory.

$C_{22}H_{22}N_2O_5$; calculated: C 66.99%; H 5.62%; N 7.10%; found: C 66.80%; H 5.64%; N 7.06%.

EXAMPLE 50

N-Acetyldehydro-3-(2-naphthyl)alanyl-L-tyrosine

Melting point: 221°-222° C. (precipitated from ethyl acetate/isopropanol with petroleum ether); $[\alpha]_D^{20} -11.6°$ (c=2; from methanol); yield: 55.7% of theory.

$C_{24}H_{22}N_2O_5$; calculated: C 68.89%; H 5.30%; N 6.70%; found: C 69.04%; H 5.37%; N 6.65%.

EXAMPLE 51

N-Benzoyldehydro-3-cyclohexylalanyl-L-tyrosine

Melting point: 126°-128° C.; $[\alpha]_D^{20} +0.8°$ (c=1; dimethylformamide); yield: 60.3% of theory.

$C_{25}H_{28}N_2O_5$; calculated: C 68.79%; H 6.46%; N 6.42%; found: C 68.59%; H 6.32%; N 6.24%.

EXAMPLE 52

N-Benzoyldehydro-3-benzyl-3-methylalanyl-L-leucine

Melting point: 98°-99° C.; $[\alpha]_D^{20} -14.1°$; yield: 39% of theory.

$C_{24}H_{28}N_2O_4$; calculated: C 70.57%; H 6.91%; N 6.86%; found: C 70.47%; H 6.74%; N 6.92%.

EXAMPLE 53

N-Benzoyldehydro-3-(2-thienyl)alanyl-L-proline

Melting point: 125° C. (ill-defined); $[\alpha]_D^{20} +2.0°$; yield: 52% of theory.

$C_{19}H_{18}N_2O_4S$; calculated: C 61.60%; H 4.90%; N 7.56%; S 8.66%; found: C 61.59%; H 4.80%; N 7.50%; S 8.79%.

EXAMPLE 54

N-Acetyldehydrophenylalanin-(1-carboxy-1-cyclopentyl) amide

Melting point: 217° C. (decomposition); yield: 50.7% of theory.

$C_{17}H_{20}N_2O_4$; calculated: C 64.54%; H 6.37%; N 8.86%; found: C 64.85%; H 6.55%; N 8.41%.

EXAMPLE 55

N-Acetyldehydro-3-(2-thienyl)analyl-L-tyrosine

Melting point: 227°-228° C.; $[\alpha]_D^{20} -36.75°$; yield: 71.06% of theory.

$C_{18}H_{18}N_2O_5S$; calculated: C 57.74%; H 4.85%; N 7.48%; S 8.56%; found: C 57.61%; H 4.84%; N 7.49%; S 8.62%.

EXAMPLE 56

N-Acetyldehydro-3-(2-thienyl)alanyl-N-methylglycine is obtained from 2-methyl-4-(2-thenylidene)-5(4H)oxazolone and N-methylglycine.

Melting point: 207°-208° C.; yield: 82.4% of theory.

$C_{12}H_{14}NO_4S$; calculated: C 51.05%; H 5.00%; N 9.92%; S 11.36%; found: C 51.19%; H 5.09%; N 9.97%; S 11.19%.

EXAMPLE 57

N-(3,4,5-Trimethoxycinnamoyl)dehydro-3-(2-thienyl)alanyl-L-tyrosine is obtained from 2-[2-(3,4,5-trimethoxyphenyl)vinyl]-4-(2-thenylidene)-5(4H)oxazolone and L-tyrosine.

Melting point: 148°-150° C.; yield: 92.2% of theory.

$C_{28}H_{28}N_2O_8S$; calculated: C 60.86%; H 5.11%; N 5.07%; S 5.80%; found: C 60.74%; H 5.15%; N 5.07%; S 5.79%.

EXAMPLE 58

N-Crotonoyldehydro-3-(2-thienyl)alanyl-L-tyrosine is obtained from 2-(1-propenyl)-4-(2-thenylidene)-5(4H)-oxazolone and L-tyrosine.

Melting point: 157° C.; yield: 51% of theory.

$C_{20}H_{20}NO_5S$; calculated: C 59.99%; H 5.03%; N 7.00%; S 8.01%; found: C 60.34%; H 4.97%; N 6.63%; S 7.51%.

EXAMPLE 59

N-Acetyldehydro-3-(5-nitrothienyl-2)alanyl-L-tyrosine is obtained from 2-methyl-4-(5-nitrothenylidene-2)-5(4H)oxazolone and L-tyrosine.

Melting point: 148°-157° C.; yield: 54.6% of theory.

$C_{18}H_{17}N_3O_7S$; calculated: C 51.55%; H 4.09%; N 10.02%; S 7.65%; found: C 51.36%; H 4.11%; N 10.01%; S 7.64%.

EXAMPLE 60

N-(2-Thenoyl)dehydro-3-(2-thienyl)alanyl-L-tyrosine is obtained from 2-(2-thienyl)-4-(2-thenylidene)-5(4H)oxazolone and L-tyrosine.

Melting point: 140°-150° C.; yield: 72% of theory.

$C_{21}H_{18}N_2O_5S_2$; calculated: C 57.00%; H 4.10%; N 6.33%; S 14.49%; found: C 57.01%; H 4.28%; N 6.35%; S 14.12%.

EXAMPLE 61

N-Crotonoyldehydro-3-(2-thienyl)alanyl-L-leucine is obtained from 2-(1-propenyl)-4-(2-thenylidene)-5(4H)oxazolone and L-leucine.

Melting point: 176° C.; yield: 73% of theory.

$C_{17}H_{22}N_2O_4S$; calculated: C 58.27%; H 6.33%; N 7.99%; S 9.15%; found: C 58.18%; H 6.26%; N 7.97%; S 9.23%.

EXAMPLE 62

N-Acetyldehydro-3-(2-thienyl)alanyl-O-methyl-L-tyrosine is obtained from 2-methyl-4-(2-thenylidene)-5(4H)oxazolone and O-methyl-L-tyrosine.

Melting point: 236° C.; yield: 90% of theory.
$C_{19}H_{20}N_2O_5S$; calculated: C 53.75%; H 5.19%; N 7.21%; S 8.25%; found: C 53.83%; H 5.36%; N 7.23%; S 8.30%.

EXAMPLE 63

N-Acetyldehydro-3-(2-thienyl)alanyl-L-tryptophan is obtained from 2-methyl-4-(2-thenylidene)-5(4H)oxazolone and L-tryptophan.

Melting point: 250° C.; yield: 43% of theory.
$C_{20}H_{19}N_3O_4S$; calculated: C 60.44%; H 4.82%; N 10.57%; S 8.07%; found: C 60.47%; H 4.88%; N 10.47%; S 8.23%.

EXAMPLE 64

N-Acetyldehydro-3-(2-thienyl)alanylglycine is obtained from 2-methyl-4-(2-thenylidene)-5(4H)oxazolone and glycine.

Melting point: 221°–223° C.; yield: 76.1% of theory.
$C_{11}H_{12}N_2O_4S$; calculated: C 49.25%; H 4.51%; N 10.44%; S 11.95%; found: C 49.14%; H 4.57%; N 10.45%; S 11.92%.

EXAMPLE 65

N-Acetyldehydro-3-(2-thienyl)alanyl-2-(4-hydroxyphenyl)-D-glycine is obtained from 2-methyl-4-(2-thenylidene)-5(4H)oxazolone and 2-(4-hydroxyphenyl)-D-glycine.

Melting point: 224°–226° C.; yield: 66.7% of theory.
$C_{17}H_{16}N_2O_5S$; calculated: C 56.66%; H 4.48%; N 7.77%; S 8.90%; found: C 56.62%; H 4.58%; N 7.63%; S 8.75%.

EXAMPLE 66

N-Benzoyldehydrophenylalanyl-L-leucylglycine 4-methoxyphenylamide is obtained from 2-phenyl-4-benzylidene-5(4H)oxazolone and L-leucylglycine 4-methoxyphenylamide.

Melting point: 211°–230° C.; yield: 50% of theory.
$C_{31}H_{34}N_3O_5$; calculated: C 68.62%; H 6.32%; N 10.35%; found: C 68.69%; H 6.33%; N 10.48%.

EXAMPLE 67

N-Acetyldehydro-3-(2-thienyl)alanyl-2-(1,4-cyclohexanedien-1-yl)-D-glycine is obtained from 2-methyl-4-(2-thenylidene)-5(4H)oxazolone and 2-(1,4-cyclohexanedien-1-yl)-D-glycine.

Melting point: 235°–240° C.; yield: 75.1% of theory.
$C_{17}H_{18}N_2O_4S$; calculated: C 58.94%; H 5.24%; N 8.09%; S 9.25%; found: C 58.79%; H 5.10%; N 7.93%; S 9.06%.

EXAMPLE 68

N-Acetyldehydro-3-(2-thienyl)alanyl-L-glutamic acid is obtained from 2-methyl-4-(thenylidene)-5(4H)oxazolone and L-glutamic acid.

Melting point: 205° C. (decomposition); yield: 76.5% of theory.
$C_{14}H_{16}N_2O_6S$; calculated: C 49.40%; H 4.74%; N 8.23%; S 9.42%; found: C 49.61%; H 4.76%; N 8.16%; S 9.59%.

EXAMPLE 69

N-Acetyldehydro-3-(2-thienyl)alanyl-L-leucine is obtained from 2-methyl-4-(2-thenylidene)-5(4H)oxazolone and L-leucine.

Melting point: 230° C.; yield: 89.5% of theory.
$C_{15}H_{20}N_2O_4S$; calculated: C 55.58%; H 6.21%; N 8.64%; S 9.88%; found: C 55.72%; H 6.27%; N 8.59%; S 9.87%.

EXAMPLE 70

N-Acetyldehydro-3-(2-thienyl)alanyl-L-phenylalanine is obtained from 2-methyl-4-(2-thenylidene)-5(4H)oxazolone and L-phenylalanine.

Melting point: >230° C.; yield: 92.6% of theory.
$C_{18}H_{18}N_2O_4S$; calculated: C 60.34%; H 5.07%; N 7.82%; S 8.93%; found: C 60.37%; H 5.04%; N 7.81%; S 8.96%.

EXAMPLE 71

N-Acetyldehydro-3-(2-thienyl)alanyl-L-β-alanine is obtained from 2-methyl-4-(2-thenylidene)-5(4H)-oxazolone and L-β-alanine.

Melting point: 186°–189° C.; yield: 78.5% of theory.
$C_{12}H_{14}N_2O_4S$; calculated: C 51.05%; H 5.00%; N 9.92%; S 11.36%; found: C 50.93%; H 5.07%; N 9.98%; S 11.44%.

EXAMPLE 72

N-Benzoyldehydrophenylalanylglycine is obtained from 2-phenyl-4-benzylidene-5(4H)oxazolone and glycine.

Melting point: 233° C. (decomposition); yield: 88.7% of theory.
$C_{18}H_{16}N_2O_4$; calculated: C 66.66%; H 4.97%; N 8.64%; found: C 66.87%; H 5.12%; N 8.54%.

EXAMPLE 73

N-Acetyldehydro-3-(2-thienyl)alanyl-DL-valine is obtained from 2-methyl-4-(2-thenylidene)-5(4H)oxazolone and DL-valine.

Melting point: 229°–230° C. (decomposition); yield: 91.5% of theory.
$C_{14}H_{18}N_2O_4S$; calculated: C 54.18%; H 5.84%; N 9.03%; S 10.33%; found: C 54.01%; H 5.82%; N 9.02%; S 10.37%.

EXAMPLE 74

N-(2-Thenoyl)dehydro-3-(2-thienyl)alanyl-2-(1,4-cyclohexanedien-1-yl)-D-glycine is obtained from 2-(2-thienyl)-4-(2-thenylidene)-5(4H)oxazolone and 2-(1,4-cyclohexanedien-1-yl)-D-glycine.

Melting point: 145°–155° C.; yield: 37.8% of theory.
$C_{20}H_{18}N_2O_4S$; calculated: C 57.95%; H 4.38%; N 6.76%; S 15.47%; found: C 57.82%; H 4.39%; N 6.57%; S 15.12%.

EXAMPLE 75

N-Acetyldehydro-3-(2-thienyl)alanyl-L-threonine is obtained from 2-methyl-4-(2-thenylidene)-5(4H)oxazolone and L-threonine.

Melting point: 262°–265° C. (decomposition); yield: 65% of theory.

$C_{13}H_{16}N_2O_5S$; calculated: C 49.99%; H 5.16%; N 8.97%; S 10.27%; found C 49.61%; H 5.24%; N 8.89%; S 10.33%.

EXAMPLE 76

N-Acetyldehydro-3-(2-thienyl)alanyl-L-aspartic acid is obtained from 2-methyl-4-(2-thenylidene)-5(4H)oxazolone and L-aspartic acid.

Melting point: 232° C. (decomposition); yield: 62.5% of theory.

$C_{13}H_{14}N_2O_6S$; calculated: 47.85%; H 4.32%; N 8.58%; S 9.83%; found: 47.70%; H 4.43%; N 8.45%; S 9.95%.

EXAMPLE 77

N-Benzoyldehydrophenylalanyl-L-tryptophan is obtained from 2-phenyl-4-benzylidene-5(4H)oxazolone and L-tryptophan.

Yield: 38.9% of theory.

$C_{27}H_{23}N_3O_4$; calculated: C 71.51%; H 5.11%; N 9.27%; found: C 71.45%; H 5.25%; N 9.12%.

EXAMPLE 78

N-(3-Trifluoromethylbenzoyl)dehydro-3-(2-thienyl)alanyl-L-leucine is obtained from 2-(3-trifluoromethylphenyl)-4-(2-thenylidene)-5(4H)oxazolone and L-leucine.

Melting point: 100°–105° C.; yield: 100% of theory.

$C_{21}H_{21}F_3N_2O_4S$; calculated: C 55.50%; H 4.66%; F 12.54%; N 6.16%; found: C 55.57%; H 4.74%; F 12.5%; N 6.10%.

EXAMPLE 79

N-(3-Trifluoromethylbenzoyl)dehydro-3-(2-thienyl)alanyl-L-phenylalanine is obtained from 2-(3-trifluoromethylphenyl)-4-(2-thenylidene)-5(4H)oxazolone and L-phenylalanine.

Melting point: 103°–107° C.; yield: 88% of theory.

$C_{24}H_{19}F_3N_2O_4S$; calculated: C 59.01%; H 3.92%; F 11.67%; N 5.74%; found: C 58.86%; H 4.01%; F 11.3%; N 5.72%.

EXAMPLE 80

N-(3-Trifluoromethylbenzoyl)dehydro-3-(2-thienyl)alanylglycine is obtained from 2-(3-trifluoromethylphenyl)-4-(2-thenylidene)-5(4H)oxazolone and glycine.

Melting point: 91°–92° C.; yield: 81% of theory.

$C_{17}H_{13}F_3N_2O_4S$; calculated: C 51.26%; H 3.29%; F 14.31%; N 7.03%; S 8.04%; found: C 51.06%; H 3.45%; F 14.30%; N 6.94%; S 8.04%.

EXAMPLE 81

N-Trifluoroacetyldehydrophenylalanyl-L-tyrosine tert.-butyl ester

The reaction is carried out in dimethylformamide without NaOH.

Melting point: 182°–183° C.; $[\alpha]_D^{20}$ −29.7° (c=1, dimethylformamide); yield: 84% of theory.

$C_{24}H_{25}F_3N_2O_5$; calculated: C 60.24%; H 5.27%; F 11.91%; N 5.86%; found: C 60.30%; H 5.30%; F 11.91%; N 5.93%.

EXAMPLE 82

N-Acetyldehydro-3-(2-thienyl)alanyl-3-(2-thienyl)-dehydroalanyl-L-tyrosine tert.-butyl ester is obtained from 2-[1-acetamido-3-(2-thienyl)vinyl]-4-(2-thenylidene)-5(4H)oxazolone and L-tyrosine tert.-butyl ester analogously to Example 81.

Melting point: 158° C.; yield: 94% of theory.

$C_{29}H_{31}N_3O_6S_2$; calculated: C 59.88%; H 5.37%; N 7.22%; S 11.03%; found: C 60.01%; H 5.41%; N 7.15%; S 11.08%.

EXAMPLE 83

N-Acetyldehydro-3-(2-thienyl)alanyl-3-(2-thienyl)-dehydroalanyl-L-tyrosine benzyl ester is obtained from 2-[1-acetamido-2-(2-thienyl)vinyl]-4-(2-thenylidene)-5(4H)oxazolone and L-tyrosine benzyl ester analogously to Example 81.

Melting point: 130° C.; yield: 83% of theory.

$C_{32}H_{29}N_3O_6S_2$; calculated: C 62.42%; H 4.75%; N 6.82%; S 10.42%; found: C 62.52%; H 4.68%; N 6.83%; S 10.40%.

EXAMPLE 84

N-Acetyldehydro-3-(2-thienyl)alanyl-3-(2-thienyl)-dehydroalanyl-L-tyrosine methyl ester is obtained from 2-[1-acetamido-2-(2-thienyl)vinyl]-4-(2-thenylidene)-5-(4H)oxazolone and L-tyrosine methyl ester analogously to Example 81.

Melting point: 155° C.; yield: 96% of theory.

$C_{26}H_{25}N_3O_6S_2$; calculated: C 57.86%; H 4.67%; N 7.79%; S 11.89%; found: C 58.08%; H 4.79%; N 7.75%; S 11.88%.

EXAMPLE 85

N-Acetyldehydro-3-(2-thienyl)alanyl-N-methyl-L-tyrosine methyl ester is obtained from 2-methyl-4-(2-thenylidene)-5(4H)oxazolone and N-methyl-L-tyrosine methyl ester analogously to Example 81.

Melting point: 102° C.; yield: 38.9% of theory.

$C_{20}H_{22}N_2O_5S \cdot H_2O$; calculated: C 58.38%; H 5.63%; N 6.81%; S 7.79%; found: C 58.28%; H 5.59%; N 6.89%; S 8.15%.

EXAMPLE 86

N-Acetyldehydro-3-(3-thienyl)alanyl-N-methyl-L-tyrosine is obtained from the above compound by boiling with NaOH. Melting point: 150°–170° C.; yield: 72.6% of theory.

$C_{19}H_{20}N_2O_5S$; calculated: C 58.75%; H 5.19%; N 7.21%; S 8.25%; found: C 58.62%; H 5.36%; N 7.08%; S 8.35%.

EXAMPLE 87

N-Acetyldehydro-3-(3-nitro-4-hydrophenyl)alanyl-L-tyrosine tert.-butyl ester is obtained from 2-methyl-4-(3-nitro-4-acetoxybenzylidene)-5(4H)oxazolone and L-tyrosine tert.-butyl ester analogously to Example 81.

Melting point: 148°–151° C.; yield: 45.5% of theory.

$C_{24}H_{27}N_3O_8$; calculated: C 59.37%; H 5.61%; N 8.66%; found: C 59.43%; H 5.71%; N 8.54%.

EXAMPLE 88

N-Acetyldehydro-3-(3-nitro-4-hydroxyphenyl)alanyl-L-tyrosine is obtained from the above compound by stirring with trifluoroacetic acid.

Melting point: 145° C.; yield: 93% of theory.
$C_{21}H_{22}N_3O_8$; calculated: C 56.76%; H 4.99%; N 9.24%; found: C 56.88%; H 5.09%; N 9.31%.

EXAMPLE 89

N-Benzoyldehydro-3-(4-pyridyl)alanyl-L-tyrosine methyl ester is obtained from 2-phenyl-4-(4-pyridinylmethylene)-5(4H)-oxazolone and L-tyrosine methyl ester analogously to Example 81.

Melting point: 155°–160° C.; yield: 33.7% of theory.
$C_{25}H_{23}N_3O_5 \cdot H_2O$; calculated: C 66.07%; H 5.32%; N 9.25%; found: C 66.17%; H 5.59%; N 9.25%.

EXAMPLE 90

N-benzoyldehydro-3-(4-pyridyl)alanyl-L-tyrosine is obtained from the above compound by boiling with dilute sodium hydroxide solution.

Melting point: 162°–166° C.; yield: 54.3% of theory.
$C_{24}H_{21}N_3O_5$; calculated: C 66.81%; H 4.91%; N 9.74%; found: C 66.63%; H 5.13%; N 9.77%.

EXAMPLE 91

N-(4-Nitrophenyl)acetyldehydro-3-(2-thienyl)alanyl-L-tyrosine methyl ester

Melting point: 218°–222° C.; yield: 55.7% of theory.
$C_{25}H_{23}N_3O_7S$; calculated: C 58.93%; H 4.55%; N 8.25%; S 6.29%; found: C 58.82%; H 4.55%; N 8.13%; S 6.11%.

EXAMPLE 92

N-(4-Nitrophenyl)acetyldehydro-3-(2-thienyl)alanyl-L-tyrosine is obtained from the above compound by boiling with dilute sodium hydroxide solution.

Melting point: 161°–166° C.; yield: 41.6% of theory.
$C_{24}H_{21}N_3O_7S$; calculated: C 58.17%; H 4.27%; N 8.48%; S 6.47%; found: C 58.26%; H 4.44%; N 8.45%; S 6.63%.

EXAMPLE 93

N-Acetyldehydro-3-(2-thienyl)alanyl-3-(2-thienyl)-dehydroalanyl-L-tyrosine tert.-butyl ester is obtained from 2-[1-acetamido-2-(2-thienyl)vinyl]-4-(2-thenylidine)-5(4H)oxazolone and L-tyrosine tert.-butyl ester analogously to Example 81.

Melting point: 158° C. (decomposition); yield: 94% of theory.
$C_{29}H_{31}N_3O_6S_2$; calculated: C 59.88%; H 5.375; N 7.22%; S 11.03%; found: C 60.01%; H 5.41%; N 7.15%; S 11.08%.

EXAMPLE 94

N-Acetyldehydro-3-(2-thienyl)alanyl-3-(2-thienyl)-dehydroalanyl-L-tyrosine is obtained from the above compound by adding glacial acetic acid/HCl.

Melting point: 189° C. (decomposition); yield: 88% of theory.

$C_{25}H_{23}N_3O_6S_2$; calculated: C 57.13%; H 4.91%; N 7.99%; S 12.20%; found: C 56.90%; H 4.63%; N 7.92%; S 12.04%.

EXAMPLE 95

N-Benzoyldehydroisoleucyl-L-tyrosine methyl ester is obtained from 2-phenyl-4-(1-methylpropylidene)-5(4H)-oxazolone and tyrosine methyl ester analogously to Example 81.

Melting point: 163°–165° C.; yield: 35.5% of theory.
$C_{33}H_{26}N_2O_5$; calculated: C 67.30%; H 6.38%; N 6.83%; found: C 67.23%; H 6.35%; N 6.82%.

EXAMPLE 96

N-(2-Thienyl)acetyldehydro-3-(2-thienyl)alanyl-L-tyrosine tert. butyl ester is obtained from 2-(2-thienylmethyl)-4-(2-thenylidene)-5(4H)-oxazolone and L-tyrosine tert.-butyl ester analogously to Example 81.

Melting point: 105° C.; yield: 85% of theory.
$C_{26}H_{28}N_2O_5S_2$; calculated: C 60.91%; H 5.50%; N 5.47%; S 12.51%; found: C 61.02%; H 5.57%; N 5.60%; S 12.36%.

EXAMPLE 97

N-(2-Thienyl)acetyldehydro-3-(2-thienyl)alanyl-L-tyrosine is obtained from the above compound by adding glacial acetic acid/hydrochloric acid.

Melting point: 110° C.; yield: 95% of theory.
$C_{22}H_{20}N_2O_5S_2$; calculated: C 57.88%; H 4.41%; N 6.14%; S 14.05%; found: C 57.64%; H 4.52%; N 6.06%; S 13.90%.

EXAMPLE 98

N-(2-Thienyl)acetyldehydro-3-(2-thienyl)alanyl-L-tyrosine benzyl ester is obtained from 2-(2-thienylmethyl)-4-(2-thenylidene)-5(4H)-oxazolone and L-tyrosine benzyl ester analogously to Example 81. Melting point: 95° C.; yield: 83% of theory.
$C_{29}H_{26}N_2O_5S_2$; calculated: C 63.71%; H 4.79%; N 5.13%; S 11.74%; found: C 63.85%; H 4.80%; N 5.06%; S 11.69%.

EXAMPLE 99

N-(2-Thienyl)acetyldehydro-3-(2-thienyl)alanyl-L-tyrosine methyl ester is obtained from 2-(2-thienylmethyl)-4-(2-thenylidene)-5(4H)-oxazolone and L-tyrosine methyl ester analogously to Example 81. Melting point: 200° C. (decomposition); yield: 80% of theory.
$C_{23}H_{22}N_2O_5S_2$; calculated: C 58.70%; H 4.71%; N 5.95%; S 13.63%; found: C 58.79%; H 4.76%; N 5.95%; S 13.50%.

EXAMPLE 100

N-Trifluoroacetyldehydrophenylalanyl-L-tyrosine

Melting point: 165°–175° C.; $[\alpha]_D^{20} -57.4°$ (c=1; dimethylformamide; yield: 91% of theory.
$C_{20}H_{17}F_3N_2O_5$; calculated: C 56.87%; H 4.06%; F 13.5%; N 6.63%; found: C 56.92%; H 4.05%; F 13.4%; N 6.61%.

EXAMPLE 101

N-Phenacetyldehydro-3-(2-thienyl)alanyl-L-tyrosine tert.-butyl ester is prepared in dimethylformamide without NaOH.

Melting point: 110°–120° C. (crude product); yield: 51.5% of theory.

This compound was further processed by stirring for ½ an hour with trifluoroacetic acid to give N-Phenacetyldehydro-3-(2-thienyl)alanyl-L-tyrosine Melting point: 135°–140° C. (decomposition); $[\alpha]_D^{20} -41°$; yield: 49% of theory.

$C_{24}H_{22}N_2O_5S$; calculated: C 63.98%; H 4.92%; N 6.22%; S 7.12%; found: C 63.79%; H 4.82%; N 6.29%; S 7.07%.

EXAMPLE 102

N-Phenacetyldehydro-3-(2-thienyl)alanyl-L-leucine

N-Phenacetyldehydro-3-(2-thienyl)alanyl-L-leucine methyl ester is formed from 4.05 g (0.015 mol) of 2-benzyl-4-(2-thenylidene)-5(4H)oxazolone and 3 g (0.0165 mol) of L-leucine methyl ester hydrochloride in dimethylformamide in the presence of triethylamine by stirring the mixture for two hours and allowing it to stand for twelve hours, diluting it with water, extracting it with ether, washing the ether extract with dilute citric acid and evaporating the dried ether solution. Melting point: 160°–161° C.; yield: 4.75 g (76.3% of theory).

4.66 g (0.011 mol) of the above compound were dissolved in 50 ml of tetrahydrofurane at 0° C., the solution was stirred with 11 ml of N NaOH at room temperature for two hours, the reaction solution was extracted with chloroform and the aqueous phase was acidified and then extracted with chloroform. 3.8 g (63.3% of theory) of N-phenacetyldehydro-3-(2-thienyl)-alanyl-L-leucine of melting point 207°–208° C. were obtained. $[\alpha]_D^{20} -45.2°$.

$C_{21}H_{24}N_2O_4S$; calculated: C 62.98%; H 6.04%; N 6.99%; S 8.00%; found: C 62.92%; H 6.02%; N 7.03%; S 7.92%.

EXAMPLE 103

N-Benzoyldehydrophenylalanyl-L-leucylglycine anilide is obtained from 2-phenyl-4-benzylidene-5(4H)oxazolone and L-leucylglycine anilide analgously to Example 102.

Melting point: 179°–180° C.; yield: 35.3% of theory.

$C_{30}H_{32}N_4O_4$; calculated: C 70.29%; H 6.29%; N 10.93%; found: C 69.44%; H 6.41%; N 10.82%.

EXAMPLE 104

N-Benzoyldehydrophenylalanyl-L-prolyl-L-leucylglycine anilide is obtained from 2-phenyl-4-benzylidene-5(4H)oxazolone and L-prolyl-L-leucylglycine amide.

Melting point: 192° C.; yield: 98% of theory.

$C_{35}H_{39}N_5O_5$; calculated: C 68.95%; H 6.45%; N 11.49%; found: C 69.03%; H 6.42%; N 11.45%.

EXAMPLE 105

N-Acetyldehydro-3-(2-thienyl)alanyl-2-methylalanine methyl ester is obtained from 2-methyl-4-(2-thenylidene)-5(4H)oxazolone and 2-methylalanine methyl ester analogously to Example 102.

Melting point: 181°–182° C.; yield 69% of theory.

$C_{14}H_{18}N_2O_4S$; calculated: C 54.18%; H 5.85%; N 9.03%; S 10.33%; found: C 54.32%; H 5.83%; N 9.12%; S 10.51%.

EXAMPLE 106

N-Acetyldehydro-3-(2-thienyl)alanyl-2-methylalanine is obtained from the above compound by boiling with dilute sodium hydroxide solution.

Melting point: 241° C. (decomposition); yield: 94% of theory.

$C_{13}H_{16}N_2O_4S$; calculated: C 52.69%; H 5.44%; N 9.45%; S 10.82%; found: C 52.64%; H 5.37%; N 9.47%; S 10.76%.

EXAMPLE 107

N-Benzoyldehydro-3-(2-thienyl)alanyl-L-tyrosine

Melting point: 135° C. (ill-defined); yield: 41.2% of theory.

$C_{23}H_{20}N_2O_5S$; calculated: C 63.29%; H 4.62%; N 6.43%; S 7.34%; found: C 63.25%; H 4.67%; N 6.37%; S 7.38%.

EXAMPLE 108

N-Benzoyldehydro-3-(2-thienyl)alanyl-L-(p-nitrophenyl)alanine

Melting point: 125° C. (ill-defined); $[\alpha]_D^{20} -67.3°$; yield: 60% of theory.

$C_{23}H_{19}N_3O_6S$; calculated: C 59.35%; H 4.11%; N 9.03%; S 6.89%; found: C 59.39%; H 4.36%; N 9.01%; S 6.71%.

EXAMPLE 109

N-Nicotinoyldehydro-3-(2-thienyl)alanyl-L-tyrosine

Melting point: 160° C. (ill-defined); $[\alpha]_D^{20} -8.35°$; yield: 50% of theory.

$C_{22}H_{19}N_3O_5S$; calculated: C 60.40%; H 4.38%; N 9.60%; S 7.33%; found: C 60.57%; H 4.58%; N 9.75%; S 7.32%.

EXAMPLE 110

N-(3-Trifluoromethylbenzoyl)dehydro-3-(2-thienyl)alanyl-L-tyrosine

Melting point: 125° C. (ill-defined); $[\alpha]_D^{20} -8.9°$; yield: 48% of theory.

$C_{24}H_{19}F_3N_2O_5S$; calculated: C 57.14%; H 3.80%; F 11.30%; N 5.55%; S 6.36%; found: C 56.95%; H 3.81%; F 11.40%; N 5.45%; S 6.45%.

EXAMPLE 111

N-Nicotinoyldehydro-3-(2-thienyl)alanyl-L-(p-nitrophenyl)alanine

Melting point: 197° C. (decomposition); $[\alpha]_D^{20} -98°$; yield: 75% of theory.

$C_{22}H_{18}N_4O_6S$; calculated: C 56.64%; H 3.89%; N 12.01%; S 6.87%; found: C 56.55%; H 3.91%; N 12.05%; S 6.89%.

EXAMPLE 112

N-Benzoyl-3-methyl-3-(2-thienyl)dehydroalanyl-L-tyrosine

Melting point: 128° C; $[\alpha]_D^{20}+15.6°$; yield: 66.7% of theory.

$C_{24}H_{22}N_2O_5S$; calculated: C 63.98%; H 4.92%; N 6.22%; S 7.12%; found: C 64.14%; H 4.93%; N 6.34%; S 7.03%.

EXAMPLE 113

N-acetyldehydro-3-(2-thienyl)alanyl-D-tyrosine

Melting point: 221°-222° C.; $[\alpha]_D^{20}+36.8°$; yield: 51.49% of theory.

$C_{18}H_{18}N_2O_5S$; calculated: C 57.74%; H 4.85%; N 7.48%; S 8.56%; found: C 57.83%; H 4.89%; N 7.44%; S 8.67%.

EXAMPLE 114

N-Cinnamoyldehydrophenylalanylglycine

Melting point: 159°-160° C.; yield: 75% of theory.
$C_{20}H_{18}N_2O_4.H_2O$; calculated: C 65.20%; H 5.47%; N 7.61; found: C 65.27%; H 5.32%; N 7.76%.

EXAMPLE 115

N-Benzoyldehydro-3-(2-thienyl)alanyl-L-phenylalanine

Melting point: 100° C.; $[\alpha]_D^{20}-4.8°$ (c=1; dimethylsulphoxide); yield: 80% of theory.

$C_{23}H_{20}N_2O_4S$; calculated: C 65.70%; H 4.79%; N 6.66%; S 7.63%; found: C 65.64%; H 5.01%; N 6.50%; S 7.41%.

EXAMPLE 116

N-Benzoyldehydro-3-(2-thienyl)alanyl-L-leucine

Melting point: 110°-120° C.; $[\alpha]_D^{20}+24.8°$ (c=1; dimethylsulphoxide); yield: 90% of theory.

$C_{20}H_{22}N_2O_4S$; calculated: C 62.16%; H 5.74%; N 7.25%; S 8.29%; found: C 62.19%; H 5.84%; N 7.20%; S 8.23%.

EXAMPLE 117

N-Acetyldehydro-3-(2-thienyl)-L-phenylalanine

Melting point: >230° C.; $[\alpha]_D^{20}-68.8°$ (c=1; dimethylsulphoxide); yield: 90% of theory.

$C_{18}H_{18}N_2O_4S$; calculated: C 60.32%; H 5.07%; N 7.82%; S 8.93%; found: C 60.37%; H 5.04%; N 7.81%; S 8.96%.

EXAMPLE 118

N-Benzoyl-3-methylphenyldehydroalanyl-L-leucine

Melting point: 102°-104° C.; $[\alpha]_D^{20}-8.1°$; yield: 75% of theory.

$C_{23}H_{26}N_2O_4$; calculated: C 70.03%; H 6.64%; N 7.10%; found: C 69.29%; H 6.48%; N 7.02%.

EXAMPLE 119

N-Cinnamoyldehydrophenylalanyl-L-tyrosine

Melting point: 172°-174° C.; $[\alpha]_D^{20}-24°$; yield: 30% of theory.

$C_{27}H_{24}N_2O_5$; calculated: C 71.04%; H 5.3%; N 6.14%; found: C 70.85%; H 5.39%; N 6.16%.

EXAMPLE 120

N-Acetyldehydro-3-(2-thienyl)alanine

Melting point 230° C. (decomposition). Preparation of the literature.

EXAMPLE 121

N-Acetyldehydro-3-(2-thienyl)alanyl-L-leucine

Melting point: >230° C.; $[\alpha]_D^{20}-11.0°$ (c=1; dimethylsulphoxide); yield: 90% of theory.

$C_{15}H_{20}N_2O_4S$; calculated: C 55.54%; H 6.21%; N 8.64%; S 9.88%; found: C 55.72%; H 6.27%; N 8.59%; S 9.87%.

EXAMPLE 122

N-Benzoyldehydroisoleucyl-L-tyrosine

Melting point: 107° C.; $[\alpha]_D^{20}-12.1°$; yield: 31.5% of theory.

$C_{22}H_{24}N_2O_5$; calculated: C 66.65%; H 6.10%; N 7.07%; found: C 66.57%; H 6.17%; N 6.90%.

EXAMPLE 123

N-Benzoyl-3-methyl-3-cinnamenyldehydroalanyl-L-tyrosine

Melting point: 130° C.; $[\alpha]_D^{20}-5.5°$; yield: 96% of theory.

$C_{28}H_{26}N_2O_5$; calculated: C 71.47%; H 5.57%; N 5.95%; found: C 71.60%; H 5.57%; N 5.87%.

EXAMPLE 124

N-Acetyldehydrophenylalanyldehydro(3-chlorophenyl)alanyl-L-tyrosine is obtained by aminolysis of 4-(3-chlorobenzylidene)-2-(1-acetamido-2-phenylethylene)-5(4H)-oxazolone with L-tyrosine.

Melting point: 191°-193° C.; $[\alpha]_D^{20}-154.3°$ (c=1; dimethylformamide); yield: 78.5% of theory.

$C_{29}H_{26}ClN_3O_6$; calculated: C 63.56%; H 4.78%; Cl 6.47%; N 7.67%; found: C 63.69%; H 4.76%; Cl 6.54%; N 7.70%.

EXAMPLE 125

N-Acetyldehydrophenylalanyldehydrotyrosine 6.09 g (0.0175 mol) of 2-(1-acetamido-2-phenylethylene)-4-(4-hydroxybenzylidene)-5(4H)-oxazolone are mixed with 46.9 ml of N NaOH and 40 ml of acetone and the mixture is stirred at room temperature for three hours. After distilling off the acetone, acidifying the aqueous reaction solution with 47.6 ml of N HCl and recrystallising the precipitate, which has separated out and been filtered off, from ethanol/petroleum ether, 3.75 g (58.6% of theory) of N-acetyldehydrophenylalanyldehydrotyrosine of melting point 202°-206° C. are obtained. Preparation in the literature.

The following compounds were prepared analogously from the corresponding oxazolones:

EXAMPLE 126

N-Acetyldehydrophenylalanyldehydro-(p-nitrophenyl)alanine

Melting point: 182° C.; yield: 56.4% of theory.
$C_{20}H_{17}N_3O_6$; calculated: C 60.76%; H 4.33%; N 10.63%; found: C 60.86%; H 4.51%; N 10.46%.

EXAMPLE 127

N-Acetyldehydrophenylalanyldehydro(4-chlorophenyl)alanine

Melting point: 177° C.; yield: 60.9% of theory.
$C_{20}H_{17}ClN_2O_4$; calculated; C 62.42%; H 4.45%; N 7.28%; Cl 9.21%; found: C 62.49%; H 4.47%; N 7.37%; Cl 9.24%.

EXAMPLE 128

N-Acetyldehydrophenylalanyldehydro(p-fluorophenyl)alanine

Melting point: 172° C.; yield: 65.27% of theory.
$C_{20}H_{17}FN_2O_4.H_2O$; calculated: C 62.17%; H 4.96%; F 4.92%; N 7.25%; found: C 62.30%; H 4.94%; F 4.70%; N 7.25%.

EXAMPLE 129

N-Acetyldehydrophenylalanyldehydro(4-dimethylaminophenyl)alanine

Melting point: 153°–155° C.; yield: 36.2% of theory.
$C_{22}H_{23}N_3O_4$; calculated: C 67.16%; H 5.89%; N 10.68%; found: C 67.03%; H 6.00%; N 10.52%.

EXAMPLE 130

N-Acetyldehydrophenylalanyldehydro(3-chlorophenyl)alanine

Melting point: 183° C.; yield: 88.4% of theory.
$C_{20}H_{17}ClN_2O_4$; calculated: C 62.42%; H 4.45%; Cl 9.21%; N 7.28%; found: C 62.54%; H 4.45%; Cl 9.23%; N 7.18%.

In the following examples, the reaction was carried out in tetrahydrofurane without NaOH.

EXAMPLE 131

N-Benzoyldehydro-3-(2-thienyl)alanyl-L-tyrosine methyl ester

Melting point: 120° C. (ill-defined); $[\alpha]_D^{20} - 4.6°$; yield: 95% of theory.
$C_{24}H_{22}N_2O_5S$; calculated: C 63.98%; H 4.92%; N 6.22%; S 7.12%; found: C 63.78%; H 4.93%; N 6.07%; S 7.02%.

EXAMPLE 132

N-Acetyldehydro-3-(2-thienyl)alanyl-L-tyrosine methyl ester

Melting point: 243°–245° C.; $[\alpha]_D^{20} - 78.1°$ (c=1; dimethylsulphoxide); yield: 65% of theory.
$C_{19}H_{20}N_2O_5S$; calculated: C 58.75%; H 5.19%; N 7.21%; S 8.26%; found: C 58.45%; H 5.35%; N 7.17%; S 8.47%.

EXAMPLE 133

N-Benzoyldehydro-3-(2-thienyl)alanyl-l-tyrosine benzyl ester is obtained from the acid and benzyl alcohol by heating to 80° C. for ½ an hour in the presence of hydrogen chloride.

Melting point: 95° C. (ill-defined); $[\alpha]_D^{20} - 2.0°$; yield: 79% of theory.
$C_{30}H_{26}N_2O_5S$; calculated: C 68.42%; H 4.98%; N 5.32%; S 6.09%; found: C 68.42%; H 4.96%; N 5.30%; S 6.02%.

EXAMPLE 134

The salt of N-acetyldehydro-3-(2-thienyl)alanine with morpholine

To 1.5 g of the dehydroamino acid, three times the amount of morpholine is added and the mixture is diluted with methanol and evaporated to dryness.

Melting point: 173° C. (decomposition); yield: 89% of theory.
$C_{13}H_{18}N_2O_4S$; calculated: C 52.4%; H 6.0%; N 9.4%; S 10.7%; found: C 52.8%; H 6.2%; N 9.4%; S 11.1%.

The following compounds are prepared analogously to Example 134:

EXAMPLE 135

The salt of N-acetyldehydro-3-(2-thienyl)alanine with methylamine

Melting point: 178° C.; yield: 99% of theory.
$C_{10}H_{14}N_2O_3S$; calculated: C 49.57%; H 5.82%; N 11.56%; S 13.24%; found: C 49.74%; H 5.92%; N 11.60%; S 13.23%.

EXAMPLE 136

The salt of N-acetyldehydro-3-(2-thienyl)alanine with 1,1-dimethylproparglyamine Melting point: 221° C. (decomposition); yield: 99% of theory.
$(C_{14}H_{18}N_2O_3S$; calculated: C 57.12%; H 6.16%; N 9.52%; S 10.89%; found: C 57.24%; H 6.21%; N 9.68%; S 11.06%.

EXAMPLE 137

The lithium salt of N-acetyldehydro-3-(2-thienyl)alanine

Melting point: >300° C.; yield: 66.08% of theory.
$C_9H_8LiNO_3S$; calculated: C 49.77%; H 3.71%; N 6.45%; S 14.76%; Li 3.21%; found: C 49.79%; H 3.92%; N 6.30%; S 14.45%; Li 3.35%.

EXAMPLE 138

The salt of N-acetyladehydro-3-(2-thienyl)alanyl-L-tyrosine with morpholine

Melting point: 136°–150° C.; yield: 69.40% of theory.
$C_{22}H_{27}N_3O_6S$; calculated: C 57.25%; H 5.90%; N 9.11%; S 6.95%; found: C 56.54%; H 6.14%; N 8.85%; S 6.42%.

EXAMPLE 139

The salt of N-acetyldehydro-3-(2-thienyl)alanyl-L-tyrosine with piperidine

Melting point: 184°–186° C.; yield: 58.80% of theory.
$C_{23}H_{29}N_3O_5S$; calculated: C 60.11%; H 6.36%; N 9.14%; S 6.98%; found: C 60.29%; H 6.27%; N 9.33%; S 7.17%.

EXAMPLE 140

The salt of N-acetyldehydro-3-(2-thienyl)alanyl-L-tyrosine with ethylenediamine

Melting point: 148°–158° C.; yield: 98.9% of theory.

$C_{38}H_{44}N_6O_{10}S_2$; calculated: C 56.42%; H 5.48%; N 10.39%; S 7.93; found: C 56.38%; H 5.64%; N 10.26%; S 7.81%.

EXAMPLE 141

The salt of N-acetyldehydro-3-(2-thienyl)alanyl-L-tyrosine with triethanolamine

Melting point: 125°–130° C.; yield: 84.1% of theory. $C_{24}H_{33}N_3O_8S$; calculated: C 55.05%; H 6.35%; N 8.03%; S 6.12%; found: C 54.77%; H 6.30%; N 7.93%; S 6.00%.

EXAMPLE 142

The salt of N-acetyldehydro-3-(2-thienyl)alanyl-L-tyrosine with DL-canavanine

Melting point: 165°–173° C.; yield: 90.9% of theory. $C_{23}H_{30}N_6O_8S$; calculated: C 50.17%; H 5.49%; N 15.27%; S 5.81%; found: C 50.02%; H 5.62%; N 15.35%; S 5.67%.

EXAMPLE 143

The salt of N-acetyldehydro-3-(2-thienyl)alanyl-L-tyrosine with L-arginine

Melting point: 125°–140° C.; yield: 79.3% of theory. $C_{24}H_{32}N_6O_7S$; calculated: C 52.54%; H 5.88%; N 15.32%; S 5.85%; found: C 52.44%; H 6.00%; N 15.31; S 5.10%.

EXAMPLE 144

The salt of N-acetyldehydro-3-(2-thienyl)alanyl-L-tyrosine with L-lysine

Melting point: 174°–182° C.; yield: 96.1% of theory. $C_{24}H_{32}N_4O_7S$; calculated: C 55.37%; H 6.20%; N 10.76%; S 6.16%; found: C 55.22%; H 6.41%; N 10.87%; S 6.04%.

The amides which follow were prepared from the corresponding methyl esters by allowing a mixture of the esters and the corresponding amines (1 mol of ester per 8 mols of amine) in methanol or tetrahydrofurane to stand and working up the mixture by evaporation and purification on silica gel (reaction time 3–340 hours).

EXAMPLE 145

N-Benzoyldehydro-3-(2-thienyl)alanyl-L-tyrosine amide

Melting point: 210° C.; $[\alpha]_D^{20} - 62.0°$; yield: 86% of theory.

$C_{23}H_{21}N_3O_4S$; calculated: C 63.43%; H 4.86%; N 9.65%; S 7.36%; found: C 63.25%; H 4.96%; N 9.59%; S 7.38%.

EXAMPLE 146

N-Benzoyldehydro-3-(2-thienyl)alanyl-L-tyrosine N'-hexylamide

Melting point: 115° C. (ill-defined); $[\alpha]_D^{20} - 63.4°$; yield: 80% of theory.

$C_{29}H_{33}N_3O_4S$; calculated: C 67.03%; H 6.40%; N 8.09%; S 6.17%; found: C 67.22%; H 6.51%; N 8.19%; S 6.08%.

EXAMPLE 147

N-Benzoyldehydro-3-(2-thienyl)alanyl-L-tyrosine N'-methylamide

Melting point: 145° C. (ill-defined); $[\alpha]_D^{20} - 61.7°$; yield: 90.2% of theory.

$C_{24}H_{23}N_3O_4S$; calculated: C 64.12%; H 5.16%; N 9.35%; S 7.13%; found: C 64.04%; H 4.99%; N 9.42%; S 7.07%.

EXAMPLE 148

N-Benzoyldehydro-3-(2-thienyl)alanyl-L-tyrosine N'-cyclohexylamide

Melting point: 110° C. (ill-defined); $[\alpha]_D^{20} - 50.9°$; yield: 44% of theory.

$C_{29}H_{31}N_3O_4S$; calculated: C 67.29%; H 6.04%; N 8.12%; S 6.19%; found: C 67.38%; H 6.33%; N 8.09%; S 5.88%.

EXAMPLE 149

N-Benzoyldehydro-3-(2-thienyl)alanyl-L-tyrosine N',N'-dimethylamide

Melting point: 130° C. (ill-defined); $[\alpha]_D^{20} - 2.2°$; yield: 13% of theory.

$C_{25}H_{25}N_3O_4S$; calculated: C 64.77%; H 5.44%; N 9.06%; S 6.92%; found: C 64.64%; H 5.41%; N 9.06%; S 6.77%.

EXAMPLE 150

N-benzoyldehydro-3-(2-thienyl)alanyl-L-tyrosine morpholide

Melting point: 120° C. (ill-defined); $[\alpha]_D^{20} - 0.7°$; yield: 22% of theory.

$C_{27}H_{27}N_3O_5S$; calculated: C 64.14%; H 4.38%; N 8.32%; S 6.34%; found: C 63.92%; H 5.53%; N 8.27%; S 6.09%.

EXAMPLE 151

N-Benzoyldehydro-3-(2-thienyl)-L-tyrosine-N'-benzylamide

Melting point: 133° C; $[\alpha]_D^{20} - 69.83°$; yield: 68% of theory.

$C_{30}H_{27}N_3O_4S$; calculated: C 63.55%; H 5.18%; N 7.99%; S 6.10%; found: C 63.65%; H 5.25%; N 8.13%; S 6.03%.

EXAMPLE 152

N-Acetyldehydro-3-(2-thienyl)alanyl-L-tyrosine 2-dimethylaminopropylamide

Melting point: 177°–179° C. (decomposition); yield: 63% of theory.

$C_{23}H_{30}N_4O_4S$; calculated: C 60.24%; H 6.59%; N 12.22%; S 6.99%; found: C 60.39%; H 6.75%; N 12.40%; S 6.89%.

EXAMPLE 153

N-Acetyldehydro-3-(2-thienyl)alanyl-L-tyrosine amide

Melting point: 147° C.; yield: 79% of theory.

$C_{18}H_{19}N_3O_4S$; calculated: C 57.89%; H 5.13%; N 11.25%; S 8.59%; found: C 57.75%; H 5.20%; N 11.09%; S 8.53%.

EXAMPLE 154

N-Acetyldehydro-3-(2-thienyl)alanyl-L-tyrosine methylamide

Melting point: 225° C.; yield: 50% of theory.
$C_{19}H_{21}N_3O_4S$; calculated C 58.90%; H 5.46%; N 10.85%; S 8.27%; found: C 58.90%; H 5.47%; N 10.85%; S 8.30%.

EXAMPLE 155

N-Benzoyldehydro-3-(2-thienyl)alanyl-L-tyrosine 6-aminohexylamide

Melting point: 122° C.; yield: 51.4% of theory.
$C_{29}H_{34}N_4O_4S$; calculated: C 65.14%; H 6.41%; N 10.48%; S 6.00%; found: C 65.04%; H 6.42%; N 10.45%; S 6.10%.

EXAMPLE 156

N-Benzoyldehydro-3-(2-thienyl)alanyl-L-tyrosine 4-aminobutylamide

Melting point: 126° C.; yield: 70% of theory.
$C_{27}H_{30}N_4O_4S$; calculated: C 64.00%; H 5.96%; N 11.06%; S 6.32%; found: C 64.28%; H 5.98%; N 10.84%; S 6.19%.

EXAMPLE 157

N-Acetyldehydro-3-(2-thienyl)alanyl-L-tyrosine hydrazide

Melting point: 240° C. (decomposition); yield: 35.3% of theory.
$C_{18}H_{20}N_4O_4S$; calculated: C 55.66%; H 5.19%; N 14.42%; S 8.25%; found: C 55.58%; H 5.28%; N 14.56%; S 8.34%.

EXAMPLE 158

N-Benzoyldehydro-3-(2-thienyl)alanyl-L-tyrosine hydrazide

Melting point: 135° C.; yield: 82.2% of theory.
$C_{23}H_{22}N_4O_4S$; calculated: C 61.32%; H 4.92%; N 12.44%; S 7.11%; found: C 61.12%; H 5.02%; N 12.38%; S 7.26%.

If instead of sodium hydroxide a corresponding amine is used, the following compounds are formed from the corresponding 5(4H)oxazolones:

EXAMPLE 159

N-Acetyldehydro-3-(2-thienyl)alanine N'-methylamide

Melting point: 183° C.; yield: 89% of theory.
$C_{10}H_{12}N_2O_2S$; calculated: C 53.55%; H 5.39%; N 12.49%; S 14.30%; found: C 53.66%; H 5.52%; N 12.52%; S 14.23%.

EXAMPLE 160

N-Acetyldehydro-3-(2-thienyl)alanine N'-1,1-dimethyl-2-propinylamide

Melting point: 197°-200° C.; yield: 36.2% of theory.
$C_{14}H_{16}N_2O_2S$; calculated: C 60.85%; H 5.84%; N 10.14%; S 11.60%; found C 60.64%; H 6.06%; N 10.08%; S 11.38%.

EXAMPLE 161

N-Acetyldehydro-3-(2-thienyl)alanine morpholide

Melting point: 159° C.; yield: 82.7% of theory.
$C_{13}H_{16}N_2O_3S$; calculated: C 55.69%; H 5.75%; N 9.99%; S 11.44%; found: C 55.80%; H 5.73%; N 10.09%; S 11.22%.

EXAMPLE 162

N-Cinnamoyldehydroalanine N'-methylamide

Melting point: 114°-118° C.; yield: 70% of theory.
$C_{19}H_{18}N_2O_2$; calculated: C 74.5%; H 5.9%; N 9.1%; found: C 74.4%; H 6.0%; N 9.0%.

EXAMPLE 163

N-Cinnamoyldehydroalanine 1,1-dimethyl-2-propinylamide

Melting point: 200°-203° C.; yield: 40% of theory.
$C_{23}H_{22}N_2O_2$; calculated: C 77.1%; H 6.2%; N 7.8%; found: C 77.1%; H 6.2%; N 8.0%.

EXAMPLE 164

N-Cinnamoyldehydroalanine morpholide

Melting point: 179°-182° C.; yield: 50% of theory.
$C_{22}H_{22}N_2O_3$; calculated: C 72.9%; H 6.1%; N 7.7%; found: C 72.8%; H 6.2%; N 7.5%.

EXAMPLE 165

N-Ethoxyacetyldehydro-3-(2-thienyl)alanine 4-methylpiperazide

Melting point: 95°-97° C.; yield: 71.4% of theory.
$C_{16}H_{23}N_3O_3S$; calculated: C 56.95%; H 6.87%; N 12.45%; S 9.50; found: C 56.79%; H 6.94%; N 12.44%; S 9.56%.

EXAMPLE 166

N-Ethoxyacetyldehydro-3-(2-thienyl)alanine anilide

Melting point: 158°-159° C. yield: 97.9% of theory.
$C_{17}H_{18}N_2O_3S$; calculated: C 61.80%; H 5.49%; N 8.48%; S 9.70%; found: C 61.90%; H 5.48%; N 8.48%; S 9.65%.

EXAMPLE 167

N-Ethoxyacetyldehydro-3-(2-thienyl)alanine cyclohexylamide

Melting point: 142°144° C.; yield: 72% of theory.
$C_{17}H_{24}N_2O_3S$; calculated: C 60.69%; H 7.19%; N 8.32%; S 9.53%; found: C 60.27%; H 7.25%; N 8.32%; S 9.42%.

EXAMPLE 168

N-Ethoxyacetyldehydro-3-(2-thienyl)alanine amide

Melting point: 145°-147° C.; yield: 50.6% of theory.
$C_{11}H_{14}N_2O_3S$; calculated: C 51.95%; H 5.55%; N 11.01%; S 12.62%; found: C 51.92%; H 5.50%; N 10.86%; S 12.66%.

EXAMPLE 169

N-Crotonoyldehydro-3-(2-thienyl)alanine 4-methylpiperazide

Melting point: 172°-173° C.; yield: 90% of theory.
$C_{16}H_{21}N_3O_2S$; calculated: C 60.16%; H 6.63%; N 13.16%; S 10.04; found: C 60.18%; H 7.04%; N 13.16%; S 9.92%.

EXAMPLE 170

N-Crotonoyldehydro-3-(2-thienyl)alanine 3-dimethylaminopropylamide

Melting point: 137°–138° C.; yield: 83% of theory.
$C_{16}H_{23}N_3O_2S$; calculated: C 59.78%; H 7.21%; N 13.07%; S 9.98%; found: C 59.44%; H 7.16%; N 13.02%; S 9.93%.

EXAMPLE 171

N-Crotonoyldehydro-3-(2-thienyl)alanine 6-aminohexylamide

Melting point: 113°–114° C.; yield: 70% of theory.
$C_{17}H_{25}N_3O_2S$; calculated: C 60.86%; H 7.51%; N 12.53%; S 9.56%; found: C 60.73%; H 7.58%; N 12.56%; S 9.37%.

EXAMPLE 172

N-Acetyldehydrophenylalanyl-3-(2-thienyl)dehydroalanine methylamide

Melting point: 226° C.; yield: 89% of theory.
$C_{19}H_{19}N_3O_3S$; calculated: C 61.77%; H 5.18%; N 11.37%; S 8.68%; found: C 61.65%; H 5.25%; N 11.6%; S 8.63%.

EXAMPLE 173

N-(3-Trifluoromethylbenzoyl)dehydro-3-(2-thienyl)alanine anilide

Melting point: 240°–243° C.; yield: 56% of theory.
$C_{21}H_{15}F_3N_2O_2S$; calculated: C 60.57%; H 3.63%; F 13.69%; N 6.73%; S 7.70%; found: C 60.55%; H 3.73%; F 13.5%; N 6.75%; S 7.71%.

EXAMPLE 174

N-(3-Trifluoromethylbenzoyl)dehydro-3-(2-thienyl)alanine 4-methylpiperazide

Melting point: 187°–188° C.; yield: 63.8% of theory.
$C_{20}H_{20}F_3N_3O_2S$; calculated: C 56.73%; H 4.76%; N 9.92%; F 13.46%; S 7.57%; found: C 56.57%; H 4.63%; N 9.98%; F 13.4%; S 7.56%.

EXAMPLE 175

N-(3-Trifluoromethylbenzoyl)dehydro-3-(2-thienyl)alanine 3-dimethylaminopropylamide Melting point: 152°–154° C.
$C_{20}H_{22}F_3N_3O_2S$; TP 5
calculated: C 56.46%; H 5.21%; N 9.88%; F 13.4%; found: C 56.55%; H 5.32%; N 10.0%; F 13.6%.

EXAMPLE 176

N-(3-Trifluoromethylbenzoyl)dehydro-3-(2-thienyl)alanine amide

Melting point: 205°–207° C.
$C_{15}H_{11}F_3N_2O_2S$; calculated: C 52.94%; H 3.26%; N 8.23%; F 16.75%; S 9.42%; found: C 53.05%; H 3.25%; N 8.26%; F 16.9%; S 9.46%.

EXAMPLE 177

N-Acetyldehydro-3-(2-thienyl)alanyl-3-methyl-3-(2-thienyl)dehydroalanine hexylamide Melting point: 110° C.; yield: 90% of theory.
$C_{23}H_{29}N_3O_3S_2$; calculated: C 60.10%; H 6.36%; N 9.14%; S 13.96%; found: C 60.20%; H 6.56%; N 9.26%; S 13.91%.

EXAMPLE 178

N-Nicotinoyl-3-(2-thienyl)dehydroalanine propargylamide

Melting point: 140°–143° C.; yield: 98% of theory.
$C_{16}H_{13}N_3O_2S \cdot H_2O$; calculated: C 58.34%; H 4.59%; N 12.76%; S 9.74%; found: C 58.21%; H 4.58%; N 13.15%; S 10.01%.

EXAMPLE 179

N-(2-Thienylacetyl)dehydro-3-(2-thienyl)alanine 3-dimethylaminopropylamide

Melting point: 143° C.; yield: 74% of theory.
$C_{18}H_{23}N_3O_2S_2$; calculated: C 57.26%; H 6.14%; N 11.13%; S 16.99%; found: C 57.41%; H 6.09%; N 11.08%; S 17.05%.

EXAMPLE 180

N-Benzoyldehydro-3-(2-thienyl)alanine 3-dimethylaminopropylamide

Melting point: 174°–176° C.; yield: 91% of theory. TP 5
$C_{19}H_{23}N_3O_2S$; calculated: C 63.84%; H 6.49%; N 11.76%; S 8.96%; found: C 63.92%; H 6.47%; N 11.91%; S 9.06%.

EXAMPLE 181

N-Benzoyldehydro-3-(2-thienyl)alanine anilide

Melting point: 231° C.; yield: 84% of theory.
$C_{20}H_{16}N_2O_2S$; calculated: C 68.94%; H 4.63%; N 8.04%; S 9.20%; found: C 69.20%; H 4.48%; N 8.03%; S 9.16%.

EXAMPLE 182

N-Benzoyldehydro-3-(2-thienyl)alanine methylamide

Melting point: 231° C. (decomposition); yield: 92% of theory
$C_{15}H_{14}N_2O_2S$; calculated: C 63.91%; H 4.93%; N 9.78%; S 11.20%; found: C 62.94%; H 5.10%; N 9.85%; S 11.30%.

EXAMPLE 813

N-Benzoyldehydro-3-(3-thienyl)alanine hexylamide

Melting point: 121° C.; yield: 95% of theory.
$C_{20}H_{24}N_2O_2S$; calculated: C 67.38%; H 6.79%; N 7.86%; S 8.99%; found: C 67.31%; H 6.85%; N 7.95%; S 8.89%.

EXAMPLE 184

N-Benzoyldehydro-3-(2-thienyl)alanine propargylamide

Melting point: 185°–186° C.; yield: 75% of theory.
$C_{17}H_{14}N_2O_2S$; calculated: C 65.79%; H 4.55%; N 9.03%; S 10.33%; found: C 65.93%; H 4.65%; N 8.88%; S 10.39%.

EXAMPLE 185

N-Benzoyldehydrophenylalanine hydrazide

Melting point: 151°–153° C.; yield: 28% of theory.
$C_{16}H_{15}N_3O_2$; TP 5
calculated: C 68.31%; H 5.37%; N 14.94%; found: C 68.14%; H 5.53%; N 14.89%.

EXAMPLE 186

N-Benzoyldehydrophenylalanine anilide

Melting point: 213°–233° C.; yield: 80% of theory. $C_{22}H_{18}N_2O_2$; calculated: C 77.17%; H 5.3%; N 8.18%; found: C 77.63%; H 5.7%; N 8.09%.

EXAMPLE 187

N-Benzoyldehydrophenylalanine methylamide

Melting point: 172°–174° C.; yield: 71% of theory. $C_{17}H_{16}N_2O_2$; calculated: C 70.6%; H 5.9%; N 9.7%; found: C 70.4%; H 5.9%; N 9.8%.

EXAMPLE 188

N-Benzoyldehydrophenylalanine 1,1-dimethylpropargylamide

Melting point: 169°–174° C.; yield: 85% of theory. $C_{21}H_{20}N_2O_2$; calculated: C 75.88%; H 6.06%; N 8.43%; found: C 75.74%; H 6.07%; N 8.36%.

EXAMPLE 189

N-Benzoyldehydrophenylalanine hexylamide

Melting point: 139°–140° C.; yield: 63% of theory. $C_{22}H_{26}N_2O_2$; calculated: C 75.4%; H 7.48%; N 7.99%; found: C 75.43%; H 7.45%; N 8.09%.

EXAMPLE 190

N-Benzoyldehydrophenylalanine cyclohexylamide

Melting point: 197°–199° C.; yield: 85% of theory. $C_{22}H_{24}N_2O_2$; calculated: C 75.83%; H 6.94%; N 8.04%; found: C 75.81%; H 7.02%; N 8.08%.

EXAMPLE 191

N-Benzoyldehydrophenylalanine morpholide

Melting point: 158°–160° C.; yield: 63% of theory. $C_{20}H_{20}N_2O_3$; calculated: C 71.41%; H 5.99%; N 8.33%; found: C 71.3%; H 6.03%; N 8.2%.

EXAMPLE 192

N-Benzoyldehydrophenylalanine 4-methoxyphenyl hydrazide

Melting point: 207°–209° C.; yield: 38% of theory. $C_{23}H_{21}N_3O_3$; calculated: C 71.3%; H 5.46%; N 10.85%; found: C 71.4%; H 5.44%; N 10.96%.

EXAMPLE 193

N-Benzoyldehydrophenylalanine 2-phenylcyclopropylamide

Melting point: 140°–143° C.; yield: 89% of theory $C_{25}H_{22}N_2O_2$; calculated: C 78.51%; H 5.80%; N 7.33%; found: C 78.52%; H 5.83%; N 7.22%.

EXAMPLE 194

N-Benzoyldehydrophenylalanine 3,4,5-trimethoxy anilide

Melting point: 209°–212° C.; yield: 72% of theory. $C_{25}H_{24}N_2O_5$; calculated: C 69.43%; H 5.59%; N 6.48%; found: C 69.3%; H 5.55%; N 6.37%.

EXAMPLE 195

N-Benzoyldehydrophenylalanine 3-dimethylaminopropylamide

Melting point: 124°–126° C.; yield: 68% of theory. $C_{21}H_{25}N_3O_2$; calculated: C 71.77%; H 7.14%; N 11.96%; found: C 71.67%; H 7.17%; N 12.13%.

EXAMPLE 196

N-Benzoyldehydrophenylalanine propargylamide

Melting point: 190°–191° C.; yield: 81% of theory. $C_{19}H_{16}N_2O_2$; calculated: C 74.98%; H 5.30%; N 9.21%; found: C 74.93%; H 5.37%; N 9.20%.

EXAMPLE 197

N-Acetyldehydro-3-(2-thienyl)alanine-2-(4-imidazolyl) ethylamide

Melting point: 105° C.; yield: 76.2% of theory. $C_{14}H_{16}N_4O_2S$; calculated: C 55.24%; H 5.30%; N 18.41%; S 10.53%; found: C 55.26%; H 5.47%; N 18.41%; S 10.30%.

EXAMPLE 198

N-Acetyldehydro-3-(2-thienyl)alanine hexylamide

Melting point: 152°–153° C.; yield: 91.8% of theory. $C_{15}H_{22}N_2O_2S$; calculated: C ;b 61.19%; H 7.53%; N 9.52%; S 10.89%; found: C 61.24%; H 7.57%; N 9.48%; S 10.98%.

EXAMPLE 199

N-Acetyldehydro-3-(2-thienyl)alanine 2-phenylcyclopropylamide

Melting point: 204° C.; yield: 82.8% of theory. $C_{18}H_{18}N_2O_2S$; calculated: C 66.23%; H 5.56%; N 8.58%; found: C 66.30%; H 5.61%; N 8.67%.

EXAMPLE 200

N-Acetyldehydro-3-(2-thienyl)alanine benzylamide

Melting point: 193°–195° C.; yield: 93.3% of theory. $C_{16}H_{16}N_2O_3S$; calculated: C 62.98%; H 5.37%; N 9.33%; S 10.67%; found: C 63.93%; H 5.31%; N 9.23%; S 10.40%.

EXAMPLE 201

N-Acetyldehydro-3-(2-thienyl)alanine 3-dimethylaminopropylamide

Melting point: 137°–139° C.; yield: 78% of theory. $C_{14}H_{21}N_3O_2S$; calculated: C 56.92%; H 7.17%; N 14.23%; S 10.85%; found: C 56.79%; H 7.09%; N 14.16%; S 10.71%.

EXAMPLE 202

N-Acetyldehydro-3-(2-thienyl)alanine piperidide

Melting point: 160°–161° C.; yield: 61.1% of theory. $C_{14}H_{18}N_2O_2S$; calculated: C 60.40%; H 6.51%; N 10.06%; S 11.52%; found: C 60.6%; H 6.48%; N 10.1%; S 11.44%.

EXAMPLE 203

N-Acetyldehydro-3-(2-thienyl)alanine 4-methylpiperazide

Melting point: 183°–184° C.; yield: 68.3% of theory. $C_{14}H_{19}N_3O_2S$; calculated: C 57.31%; N 6.53%; N 14.32%; S 10.93%; found: C 57.40%; H 6.46%; N 14.49%; S 10.96%.

EXAMPLE 204

N-Acetyldehydro-3-(2-thienyl)alanine 4-phenylpiperazide

Melting point: 197° C.; yield: 64.8% of theory. $C_{19}H_{21}N_3O_2S$; calculated: C 64.20%; H 5.95%; N 11.82%; S 9.02%; found: C 64.09%; H 5.94%; N 11.84%; S 9.06%.

EXAMPLE 205

N-Crotonyldehydro-3-(2-thienyl)alanine 4-hydroxyanilide

Melting point: 245° C.; yield: 53% of theory. $C_{17}H_{10}N_2O_3S$; calculated: C 62.18%; H 4.92%; N 8.53%; S 9.76%; found: C 61.97%; H 5.23%; N 8.57%; S 9.65%.

EXAMPLE 206

N-Acetyldehydro-3-(2-thienyl)alanine 4-(2-hydroxyethyl)-piperazide

Melting point: 227°–230° C.; yield: 80.5% of theory. $C_{15}H_{21}N_3O_3S$; calculated: C 55.71%; H 6.59%; N 12.99%; S 9.91%; found: C 55.68%; H 6.54%; N 12.97%; S 9.64%.

EXAMPLE 207

N-Acetyldehydro-3-(2-thienyl)alanine amide

Melting point: 189° C.; yield: 76.2% of theory. $C_9H_{10}N_2O_2S$; calculated: C 51.41%; H 4.79%; N 13.32%; S 15.25%; found: C 51.34%; H 4.88%; N 13.33%; S 15.42%.

EXAMPLE 208

N-Acetyldehydro-3-(2-thienyl)alanine 2,2-dimethylhydrazide

Melting point: 174°–175° C.; yield: 59.3% of theory. $C_{11}H_{15}N_3O_2S$; calculated: C 52.15%; H 5.97%; N 16.59%; S 12.66%; found: C 52.09%; H 6.00%; N 16.69%; S 12.50%.

EXAMPLE 209

N-Acetyldehydro-3-(2-thienyl)alanine anilide

Melting point: 95°–97° C.; yield: 73.4% of theory. $C_{15}H_{14}N_2O_2S$; calculated: C 62.92%; H 4.93%; N 9.78%; S 11.20%; found: C 62.85%; H 4.99%; N 9.83%; S 11.32%.

EXAMPLE 210

N-Acetyldehydro-3-(2-thienyl)alanine 4-methylcyclohexylamide

Melting point: 195°–197° C.; yield: 57.4% of theory. $C_{16}H_{22}N_2O_2S$; calculated: C 62.71%; H 7.24%; N 9.14%; S 10.47%; found: C 62.73%; H 7.37%; N 8.99%; S 10.53%.

EXAMPLE 211

N-Acetyldehydro-3-(2-thienyl)alanine 3-morpholinopropylamide

Melting point: 135°–137° C.; yield: 48.9% of theory. $C_{16}H_{23}N_3O_3S$; calculated: C 56.95%; H 6.87%; N 12.45%; S 9.51%; found: C 56.92%; H 6.87%; N 12.30%; S 9.59%.

EXAMPLE 212

N-Acetyldehydro-3-(2-thienyl)alanine 1-phenylethylamide

Melting point: 171°–173° C.; yield: 50.9% of theory. $C_{17}H_{18}N_2O_2S$; calculated: C 64.94%; H 5.77%; N 8.91%; S 10.20%; found: C 65.14%; H 5.91%; N 8.89%; S 10.30%.

EXAMPLE 213

N-Acetyldehydro-3-(2-thienyl)alanine 3-carboxypropylamide

Melting point: 195°–197° C.; yield: 65.9% of theory. $C_{13}H_{16}N_2O_4S$; calculated: C 52.69%; H 5.44%; N 9.45%; S 10.82%; found: C 52.87%; H 5.55%; N 9.54%; S 10.98%.

EXAMPLE 214

N-Acetyldehydro-3-(2-thienyl)alanine hydrazide

Melting point: 170° C.; yield: 75.5% of theory. $C_9H_{11}N_3O_2S \cdot H_2O$ calculated: C 44.43%; H 5.39%; N 17.27%; S 13.18%; found: C 44.21%; H 5.37%; N 17.30%; S 13.26%.

EXAMPLE 215

N-Acetyldehydro-3-(2-thienyl)alanine 2-sulphonic acid ethylamide

Melting point: 192°–194° C.; yield: 68.7% of theory. $C_{11}H_{14}N_2O_5S_2$; calculated: C 41.50%; H 4.42%; N 8.80%; S 20.14%; found: C 41.36%; H 4.60%; N 8.73%; S 19.99%.

EXAMPLE 216

N-Acetyldehydro-3-(2-thienyl)alanine 1-ethinylcyclohexylamide

Melting point: 223°–224° C.; yield: 82.5% of theory. $C_{17}H_{20}N_2O_2S$; calculated: C 64.54%; H 6.37;1 %; N 8.86%; S 10.12%; found: C 64.37%; H 6.26%; N 8.70%; S 10.24%.

EXAMPLE 217

N-Acetyldehydro-3-(2-thienyl)alanine benzyloxyamide

Melting point: 142°–144° C.; yield: 47.5% of theory. $C_{16}H_{16}N_2O_3S$; calculated: C 60.74%; H 5.10%; N 8.86%; S 10.13%; found: C 60.60%; H 5.15%; N 8.99%; S 10.04%.

EXAMPLE 218

N-Acetyldehydro-3-(2-thienyl)alanine 2-hydroxyethylamide phosphate

Melting point: 180°–182° C.; yield: 35.9% of theory $C_{11}H_{15}N_2O_6PS \cdot H_2O$; calculated: C 37.50%; H 4.86%; N 7.95%; P 8.79%; S 9.11%; found: C 36.96%; H 4.78%; N 7.99%; P 8.69%; S 8.91%.

EXAMPLE 219

N-Acetyldehydro-3-(2-thienyl)alanine morpholide

Melting point: 159° C.; yield: 82.7% of theory. $C_{13}H_{16}N_2O_3S$; calculated: C 55.69%; H 5.75%; N 9.99%; S 11.22%; found: C 55.80%; H 5.73%; N 10.09%; S 11.22%.

EXAMPLE 220

N-Acetyldehydro-3-(2-thienyl)alanine propargylamide

Melting point: 202°–204° C.; yield: 72% of theory. $C_{12}H_{12}N_2O_2S$; calculated: C 58.05%; H 4.87%; N 11.28%; S 12.91%; found: C 57.96%; H 4.9%; N 11.33%; S 12.96%.

EXAMPLE 221

N-Acetyldehydro-3-(2-thienyl)alanine 3,4,5-trimethoxyanilide

Melting point: 203°–205° C.; yield: 51.3% of theory $C_{18}H_{20}N_2O_5S$; calculated: C 57.43%; H 5.36%; N 7.44%; S 8.52%; found: C 57.50%; H 5.32%; N 7.39%; S 8.63%.

EXAMPLE 222

N-acetyldehydro-3-(2-thienyl)alanine 2-(benzothiazol-2-yl)-hydrazide

Melting point: 183°–185° C.; yield: 22% of theory. $C_{16}H_{14}N_4O_2S_2$; calculated: C 53.61%; H 3.94%; N 15.63%; S 17.89%; found: C 53.41%; H 4.06%; N 15.45%; S 17.89%.

What is claimed is:

1. A pharmaceutical composition containing as an active ingredient an effective amount of 1 to 100 mg of a compound which is a dehydrooligopeptide of the following general formula or its salt

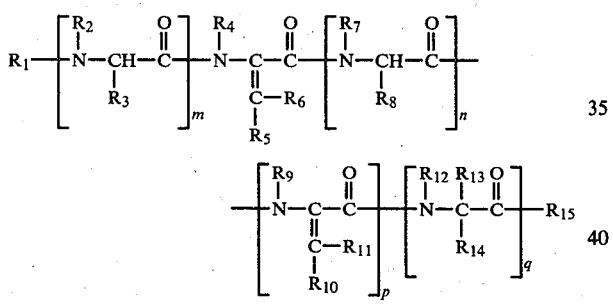

in which $R_1$ is hydrogen; alkanoyl having from 2 to 6 carbon atoms; benzoyl or naphthoyl each unsubstituted or substituted by from 1 to 3 halogen atoms or by trifluoromethyl; heteroaryl having from 5 to 7 ring members and containing from 1 to 3 hetero-atoms which are the same or different and each of which is nitrogen, sulfur or oxygen and on which there is a carbonyl group;

each of $R_2$, $R_7$ and $R_{12}$ is a hydrogen;

each of $R_3$, $R_8$ and $R_{13}$ is hydrogen; straight chain or branched alkyl having from 1 to 6 carbon atoms; phenylalkyl having from 1 to 4 carbon atoms, unsubstituted or substituted by one or more halogen atoms, nitro, hydroxyl, methoxy or alkyl having from 1 to 4 carbon atoms;

each of $R_4$ and $R_9$ is hydrogen;

each of $R_5$, $R_{10}$ and $R_{14}$ is hydrogen or alkyl having from 1 to 6 carbon atoms;

$R_7$ and $R_8$, taken together, form a divalent alkylene chain having three or four carbon atoms;

each of $R_6$ and $R_{11}$ is phenyl or naphthyl, unsubstituted or substituted by halogen atoms;

a heterocyclic radical having from 5 to 7 ring members and 1 to 2 hetero-atoms each of which is nitrogen, sulphur or oxygen, and is unsubstituted or substituted by halogen atoms or by nitro; or alkyl having from 1 to 6 carbon atoms; $R_6$ taken together with $R_5$ and the carbon atoms, at the double bond, linking them, form, a cycloalkylidene or cycloalkylidene ring, having from 3 to 7 carbon atoms; and $R_{15}$ is hydroxyl, hydrazinyl which is unsubstituted or substituted by lower alkyl, straight-chain or branched, mono or di-(alkyl- or alkenyl-) amino having from 1 to 6 carbon atoms in each alkyl or alkenyl moiety and is unsubstituted or substituted by amino, lower mono- or dialkylamino;

m, n, p and q are the same or different and each represents a figure 0 or 1, with the proviso that m, n, p and q may not all be 1 at the same time and an inert pharmaceutical carrier.

2. A pharmaceutical composition according to claim 1, wherein $R_1$ is

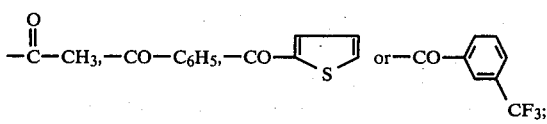

$R_2$, $R_3$, $R_4$ are each hydrogen;
$R_5$ is hydrogen or methyl;
$R_6$ is

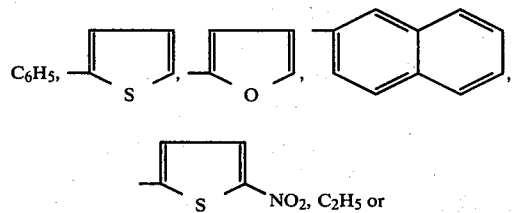

$R_6$ taken together with $R_5$ and the carbon atoms, at the double bond linking them, is cyclohexylidene or cyclohexenylidene;
$R_7$ is hydrogen;
$R_8$ is

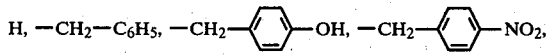

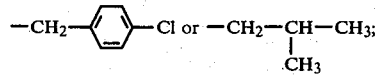

$R_7$ and $R_8$, taken together, form the —$CH_2$—$CH_2$—$CH_2$— radical;
$R_9$ is hydrogen
$R_{10}$ is hydrogen;
$R_{11}$ is

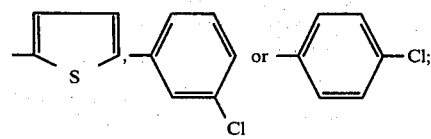

$R_{12}$ is hydrogen;

$R_{13}$ is

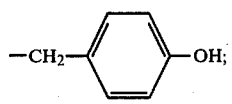

$R_{14}$ is hydrogen;
$R_{15}$ is

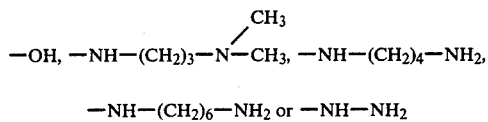

$m = 0$; and $n$, $p$ and $q$ are each 0 or 1.

3. A pharmaceutical composition according to claim 1 or 2 wherein the effective amount of active ingredient is 2 to 40 mg.

4. A pharmaceutical composition of claim 1 consisting essentially of, as an active ingredient an amount of a compound as defined in claim 1 effective for histologic action, and a sterile or isotonic aqueous carrier therefor.

5. A composition according to claim 1 or 2 containing from 1 to 90% of the said active ingredient by weight.

6. A medicament in unit dosage form comprising a composition of claim 1.

7. A medicament of claim 6 in the form of ampoules.

8. A composition according to claim 2 in which the dehydrooligopeptide is N-Acetyldehydrophenylalanine.

9. A composition according to claim 2 in which the dehydrooligopeptide is N-Acetyldehydrophenylalanyl-L-(p-nitrophenyl) alanine.

10. A composition according to claim 2 in which the dehydrooligopeptide is N-Acetyldehydro-3-(2-furyl)analyl-L-tyrosine.

11. A composition according to claim 2 in which the dehydrooligopeptide is N-Acetyldehydro-3-cinnamenylalanyl-L-tyrosine.

12. A composition according to claim 2 in which the dehydrooligopeptide is N-Acetyldehydro-3-(2-thienyl)analyl-L-tyrosine.

13. A composition according to claim 2 in which the dehydrooligopeptide is N-Acetyldehydrophenylalanyl-dehydrotyrosine.

14. A composition according to claim 2 in which the dehydrooligopeptide is N-Acetyldehydrophenylalanyl-dehydro(4-chlorophenyl) alanine.

* * * * *